United States Patent
Alitalo et al.

(10) Patent No.: US 10,400,035 B2
(45) Date of Patent: Sep. 3, 2019

(54) METHODS OF PROTECTING A SOLID ORGAN TRANSPLANT TISSUE WITH ANGIOPOIETIN-2 ANTIBODIES

(71) Applicants: MedImmune, LLC, Gaithersburg, MD (US); University of Helsinki, Helsinki (FI)

(72) Inventors: Kari Alitalo, Helsinki (FI); Simo Syrjala, Helsinki (FI); Karl Lemstrom, Helsinki (FI); Ching Ching Leow, Gaithersburg, MD (US); Ronald Herbst, Gaithersburg, MD (US); Jane Connor, Gaithersburg, MD (US)

(73) Assignees: MedImmune, LLC, Gaithersburg, MD (US); University of Helsinki, Helsinki (FI)

( * ) Notice: Subject to any disclaimer, the term of this patent is extended or adjusted under 35 U.S.C. 154(b) by 0 days.

(21) Appl. No.: 15/820,943

(22) Filed: Nov. 22, 2017

(65) Prior Publication Data

US 2018/0215818 A1     Aug. 2, 2018

Related U.S. Application Data

(63) Continuation of application No. 15/010,253, filed on Jan. 29, 2016, now abandoned, which is a continuation of application No. 14/383,377, filed as application No. PCT/US2013/029637 on Mar. 7, 2013, now abandoned.

(60) Provisional application No. 61/608,314, filed on Mar. 8, 2012, provisional application No. 61/638,303, filed on Apr. 25, 2012.

(51) Int. Cl.
| | |
|---|---|
| A61K 39/395 | (2006.01) |
| A61P 37/06 | (2006.01) |
| C07K 16/22 | (2006.01) |
| C07K 14/515 | (2006.01) |
| A61K 39/00 | (2006.01) |

(52) U.S. Cl.
CPC .......... *C07K 16/22* (2013.01); *A61K 39/3955* (2013.01); *A61P 37/06* (2018.01); *A61K 2039/505* (2013.01); *C07K 14/515* (2013.01); *C07K 2317/33* (2013.01); *C07K 2317/565* (2013.01); *C07K 2317/76* (2013.01); *C12N 2799/027* (2013.01)

(58) Field of Classification Search
None
See application file for complete search history.

(56) References Cited

U.S. PATENT DOCUMENTS

| 6,455,035 B1 | 9/2002 | Suri et al. |
| 2010/0221243 A1 | 9/2010 | Sukhatme et al. |
| 2011/0044998 A1* | 2/2011 | Bedian .............. A61K 39/39558 424/158.1 |
| 2011/0104150 A1 | 5/2011 | Tedder et al. |
| 2011/0293601 A1 | 12/2011 | Heffernan et al. |

OTHER PUBLICATIONS

Edwards et al (2003. J Mol Biol. 334: 103-118).*
Ferrara et al (2015. mAbs. 7(1): 32-41).*
European Search Report for corresponding EP13758582.4.
Fam, Neil P. et al., 2010, "Increased myocardial expression of angiopoietin-2 in patients undergoing urgent surgical revascularization for acute coronary syndromes", Canadian Journal of Cardiology, 26(7):365-370.
International Search Report for corresponding PCT/US13/29637 dated May 28, 2013.
Luft, Thomas et al., 2011, "Steroid-refractory GVHD: T-cell attack within a vulnerable endothelial system", Blood, 118(6):1685-1692.
Nykänen, Antti I. et al., 2003, "Angiopoietin-1 Protects Against the Development of Cardiac Allograft Arteriosclerosis", Circulation, 107:1308-1314.
Shyu, Kou-Gi et al., 2003, "Increased expression of angiopoietin-2 and Tie2 receptor in a rat model of myocardial ischaemia/reperfusion", Clinical Science, 105:287-294.
Slotta, JE, et al., 2007, "Blockade of Ang-2 reduces the endotoxin-mediated microvascular dysfuction of the liver", 124th Congress of the German Society of Surgery,Meeting Absttract.
Syrjälä, S.O. et al., 2014, "Angiopoietin-2 Inhibition Prevents Transplant Ischemia-Reperfusion Injury and Chronic Rejection in Rat Cardiac Allografts", American Journal of Transplantation, 14:1096-1108.
Yu, Li et al., 2010, "Endogenous toll-like receptor ligands and their biological significance", J. Cell. Mol. Med. 14(11):2592-2603.
Written Opinion for corresponding PCT/US13/29637 dated May 28, 2013.

* cited by examiner

*Primary Examiner* — Zachary C Howard

(57) ABSTRACT

The disclosure is directed to methods and uses of antibodies or antigen-binding fragments thereof against Angiopoietin-2 (Ang-2). Specifically, the disclosure is direct to the use of anti-Ang2 antibodies or antigen-binding fragments thereof for treating ischemia. The methods disclosed are useful for reducing microvascular permeability, increasing microvascular perfusion, reducing inflammation in a tissue, and treating or ameliorating diseases associated with ischemia and/or reperfusion injury. The disclosed methods are also useful for protecting solid organ transplant tissue and treating or preventing chronic tissue transplant rejection.

4 Claims, 17 Drawing Sheets
Specification includes a Sequence Listing.

METHODS OF PROTECTING A SOLID ORGAN TRANSPLANT TISSUE WITH ANGIOPOIETIN-2 ANTIBODIES

CROSS REFERENCE TO RELATED APPLICATIONS

This application claims priority to U.S. Provisional Application No. 61/608,314, filed Mar. 8, 2012 and U.S. Provisional Application No. 61/638,303, filed Apr. 25, 2012 which is incorporated by reference in their entirety.

SEQUENCE LISTING

The content of the electronically submitted sequence listing in ASCII text file (Name: "SEQIDListing.ascii.txt"; Size: 14,280 bytes; and Date of Creation: Apr. 24, 2012) filed with the application is incorporated herein by reference in its entirety.

BACKGROUND OF THE INVENTION

Field of the Invention

The invention relates to methods and uses for antibodies or antigen-binding fragments thereof against Angiopoietin-2 (Ang-2). Aspects of the invention relate to use of anti-Ang2 antibodies or antigen-binding fragments thereof for treating ischemia. The methods disclosed herein are useful for reducing microvascular permeability in a tissue; increasing microvascular perfusion in a tissue; reducing inflammation in a tissue; and treating or ameliorating diseases associated with ischemia and/or reperfusion injury. The disclosed methods are also useful for protecting solid organ transplant tissue and treating or preventing chronic tissue transplant rejection, e.g., treating or preventing ischemic reperfusion injury and microvascular dysfunction in cardiac allografts.

Background

Angiopoietins were discovered as ligands for Ties, a family of tyrosine kinases that is selectively expressed within the vascular endothelium (Yancopoulos et al., Nature 407:242-48 (2000)). There are now at least four members of the angiopoietin family: Angiopoietin-1, -2, -3 and -4. Ang-3 and Ang-4 represent widely diverged counterparts of the same gene locus in mouse and man (Kim et al., FEBS Let, 443:353-56 (1999); Kim et al., J Biol Chem 274:26523-28 (1999)). Ang-1 and Ang-2 are endothelial cell (EC)-specific growth factors, acting through the same tyrosine kinase receptor, Tie2 (1-3). Ang-1 and Ang-2 were originally identified in tissue culture experiments as an agonist and an antagonist, respectively (Davis et al., Cell 87:1161-69 (1996); Maisonpierre et al., Science 277:55-60 (1997)). All of the known angiopoietins bind primarily to Tie2, and both Ang-1 and -2 bind to Tie2 with an affinity of 3 nM (Kd) (Maisonpierre et al., Science 277:55-60 (1997)). Ang-1 was shown to support EC survival and to promote endothelium integrity (Davis et al., Cell 87:1161-69 (1996); Kwak et al., FEBS Lett 448:249-53 (1999); Suri et al., Science 282:468-71 (1998); Thurston et al., Science 286: 2511-14 (1999); and Thurston et al., Nat. Med. 6:460-63 (2000)), whereas Ang-2 had the opposite effect and promoted blood vessel destabilization and regression in the absence of the survival factors VEGF or basic fibroblast growth factor (Maisonpierre et al., Science 277:55-60 (1997)).

Angiopoietins-1 and -2 (Ang1, 2) are endothelial cell specific growth factors with context-dependent effects on their receptor, Tie2, including Ang-1 stabilization and Ang-2 destabilization of endothelial cell-cell junctions in mature vessels. Ang1 is constitutively secreted by pericytes and smooth muscle cells (SMCs) that are associated with blood vessels, and Ang1 has an indispensable role in embryonic vascular development and vessel maturation. Knocking Ang1 out, even heart-specifically, is fatal (4-6). Besides its role in embryogenesis, Ang1 also stabilizes immature and leaky vessels by promoting interactions between the endothelial cells (ECs) and perivascular structures and by regulating the endothelial cytoskeleton. Ang1 reduces vascular leakage and infarct size in ischemic murine brain model (7). A cartilage oligomeric matrix protein-Ang1 fusion, a soluble and stable variant of native Ang1 engineered to have higher activity, reduces endotoxemia-induced acute kidney injury, as well as experimental IRI-induced acute kidney injury (8), (9), (10).

In contrast, Ang-2 selectively competes with Ang-1 for binding to the Tie2 receptor and has a context dependent effect on the receptor (3, 11-13). Ang-2 is an agonist or antagonist depending on the context. Ang2 is stored together with von Willebrand factor, P-selectin, and endothelin-1 (ET-1) in Weibel-Palade bodies in the EC, and is released in response to homeostatic reactions such as inflammation and coagulation (14). Ang-2 is released in response to stress, such as inflammatory stimuli. However, Ang-2 has the ability to enhance neovascularization and to promote EC survival or increase vascular permeability (15-17). Furthermore, Ang-2 production is increased in hypoxic EC and in early phases of angiogenesis, it is involved in vessel destabilization. Induction of Ang-2 in the absence of vascular endothelial growth factor (VEGF) leads to endothelial apoptosis, while in the presence of VEGF, it promotes angiogenesis. The duration of Ang-2 exposure appears to have differing effects on vascular integrity in hindlimb ischemia models. For example, transient exposure appears to demonstrate a neovascularization role for Ang-2 (18) and extended exposure to Ang-2 appears to increase inflammation and vascular leakage (19). Ang-2 mRNA expression and protein levels are increased after experimental murine myocardial ischemia-reperfusion injury (IRI) (20). The specific role of Ang1/Ang2 axis in ischemia-reperfusion injury is not yet fully elucidated.

Hypothermic preservation is the gold standard of preoperative allograft treatment in solid organ transplantation. The restoration of blood flow following hypothermic preservation can result in profound IRI and microvascular dysfunction as well as the activation of innate immune responses, which is linked to the development of chronic rejection in solid organ transplantation. IRI can initiate pathological immune responses through the hypoxia response and release of endogenous danger molecules such as biglycan, hyaluronan and high mobility group box-1 (HMGB1) protein (21-23). These danger/damage-associated molecular patterns (DAMPs) ligate to Toll-like receptors (TLRs) and form a link between the innate immunity and the activation of the adaptive immunity that can ultimately be detrimental for the cardiac allograft and the patient (24, 25). Current organ preservation solutions fail to eliminate IRI completely, hence, finding additional methods of organ protection is needed.

While reperfusion is favorable in terms of myocardial salvage, it can result in additional cardiac damage, e.g., IRI. IRI has been associated with worsening or expansion of the prior ischemic damage resulting in microvascular dysfunction arising from endothelial cell damage, stunning, reperfusion arrhythmias, and myocyte death; a contributor to these effects is free radical generation. Thus, reperfusion injury remains a major therapeutic challenge. IRI is an inevitable factor in cardiac surgery and clinical transplantation, and new ways of its primary prevention and cardiac preservation are actively being investigated. IRI is associated with disruption of vascular endothelial integrity, EC damage and subsequent pathological remodeling leading to chronic rejection.

Thus, there is a need to develop methods for treating ischemic diseases, e.g., ischemia-reperfusion injury; reducing microvascular permeability in a tissue; increasing microvascular perfusion in a tissue; reducing inflammation in a tissue; and treating or ameliorating diseases associated with ischemia and/or reperfusion. Furthermore, there is a need to develop methods to protect solid organ transplant tissue and methods of treating or preventing chronic tissue transplant rejection.

Citation or discussion of a reference herein shall not be construed as an admission that such is prior art to the present invention.

BRIEF SUMMARY OF THE INVENTION

In certain aspects, the invention is directed to a method for reducing microvascular permeability in a tissue, comprising administering a therapeutically effective amount of an anti-Ang2 antibody or antigen-binding fragment thereof to a tissue in need thereof.

In another aspect, the invention is directed to a method for increasing microvascular perfusion in a tissue, comprising administering a therapeutically effective amount of an anti-Ang2 antibody or antigen-binding fragment thereof to a tissue in need thereof.

In another aspect, the invention is directed to a method for reducing inflammation in a tissue, comprising administering a therapeutically effective amount of an anti-Ang2 antibody or antigen-binding fragment thereof to a tissue in need thereof.

In another aspect, the invention is directed to a method for protecting a solid organ transplant tissue, comprising administering an effective amount of an anti-Ang2 antibody or antigen-binding fragment thereof to an allograft.

In another aspect, the invention is directed to a method for preventing chronic rejection, comprising administering a therapeutically effective amount of an anti-Ang2 antibody or antigen-binding fragment thereof to an allograft.

In another aspect, the invention is directed to a method for treating chronic allograft vasculopathy (CAV) in a subject comprising administering a therapeutically effective amount of an anti-Ang2 antibody or antigen-binding fragment thereof to an allograft.

In certain embodiments, the tissue is selected from the group consisting of heart, kidney, brain, smooth muscle, and intestine tissue. In some embodiments, the tissue is an allograft. In some embodiments, the allograft is a cardiac allograft. In certain embodiments, the tissue or allograft is at risk for or has suffered from ischemic reperfusion injury. In certain embodiments, the allograft is perfused with the anti-Ang2 antibody or antigen-binding fragment thereof.

In another aspect, the invention is directed to a method for treating or ameliorating myocardial ischemia, comprising administering a therapeutically effective amount of an anti-Ang2 antibody or antigen-binding fragment thereof to a subject in need thereof.

In another aspect, the invention is directed to a method for treating an IRI-induced inflammatory response in a subject comprising administering a therapeutically effective amount of an anti-Ang2 antibody or antigen-binding fragment thereof to the subject in need thereof.

In certain embodiments, administration of the anti-Ang2 antibody or antigen-binding fragment thereof reduces the immunoreactivity of VCAM-1.

In certain embodiments, the anti-Ang2 antibody or antigen-binding fragment thereof neutralizes Ang-2.

In certain embodiments, the anti-Ang2 antibody or antigen-binding fragment thereof preferentially binds Ang-2 over Ang-1.

In certain embodiments, the anti-Ang2 antibody or antigen-binding fragment thereof is an antibody that binds to and neutralizes Ang-2, but does not bind to Ang-1.

In certain embodiments, the anti-Ang2 antibody or antigen-binding fragment thereof comprises a variable light chain (VL) comprising CDRs 1-3 of SEQ ID NO: 3, 4, 5, 6, or 8 and a variable heavy chain (VH) comprising CDRs 1-3 of SEQ ID NO: 7. In some embodiments, the VL comprises the amino acid sequence of SEQ ID NO: 3, 4, 5, 6, or 8 and the VH comprises the amino acid sequence of SEQ ID NO: 7. In some embodiments, the anti-Ang2 antibody or antigen-binding fragment thereof is Ang-2 antibody binds to the same epitope as MEDI1/5, MEDI2/5, MEDI3/5, MEDI4/5, or MEDI6/5.

In certain embodiments, the anti-Ang2 antibody or antigen-binding fragment thereof is Ang-2 antibody competitively inhibits binding of MEDI1/5, MEDI2/5, MEDI3/5, MEDI4/5, or MEDI6/5 to Ang-2.

In certain embodiments, the anti-Ang2 antibody or antigen-binding fragment thereof is Ang-2 antibody MEDI1/5 or a derivative thereof.

In certain embodiments, the anti-Ang2 antibody or antigen-binding fragment thereof is administered in a single dose. In some embodiments, the anti-Ang2 antibody or antigen-binding fragment thereof is administered preoperatively. In some embodiments, the anti-Ang2 antibody or antigen-binding fragment thereof is administered to the allograft donor, to the allograft or to the allograft recipient.

In certain embodiments, the anti-Ang2 antibody or antigen-binding fragment thereof reduces expression of VEGF, TGFβ, or both.

DETAILED DESCRIPTION OF THE INVENTION

Figure 1:
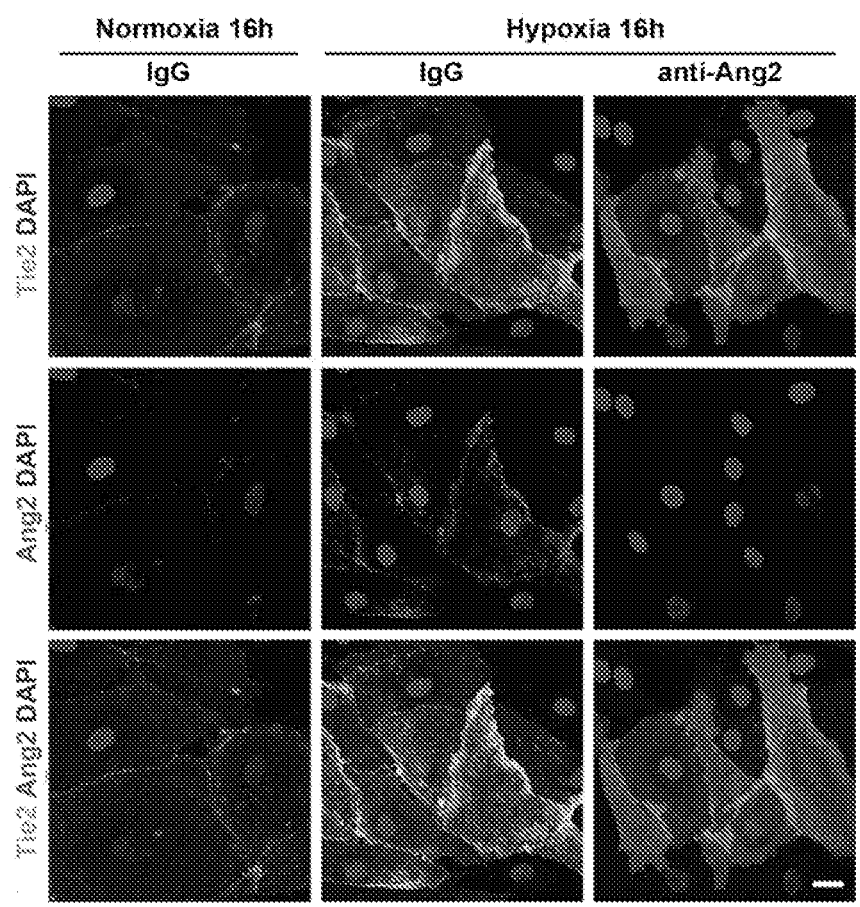
FIG. 1 shows hypoxia induces Ang2 deposition in endothelial cell-cell junctions. Human dermal blood microvascular cells (BECs) transfected with Tie2-GFP retrovirus were subjected to normoxia or hypoxia (1% O2) 5 hours after plating for 16 hours in the presence of control-IgG or anti-Ang2 antibody (MEDI1/5) (2 µg/ml). Immunofluorecent staining shows the localization of Tie2 and Ang2; DAPI indicates nuclei. (Scale bars=20 µm).
Figure 2:
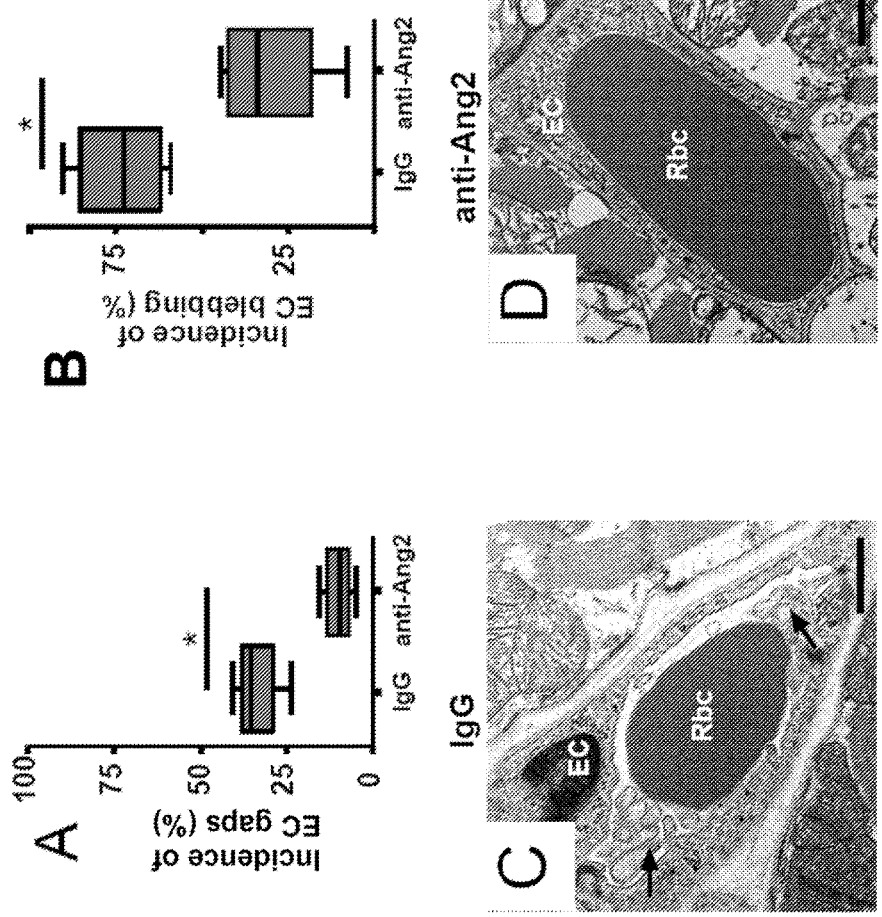
FIG. 2 shows intracoronary perfusion with anti-Ang2 antibody (MEDI1/5), and not control-IgG, stabilizes rat cardiac allograft endothelium during preservation. (A) Shows the incidence of EC gaps (%) in microvascular endothelial cell (EC)-EC junctions determined by transmission electron microscopy in non-transplanted rat cardiac allografts. (B) Shows the incidence of EC blebbing (%). (C-D) Show representative images of EC-EC gaps and blebbing in transmission electron microscopy: red arrows indicate gaps in EC-EC junctions, black arrows indicate EC blebbing. n=5 per group. The Mann-Whitney U test was used to compare anti-Ang2 and IgG treatment. Data are given by box plots showing the upper extreme (excluding outliers), upper quartile, median, lower quartile, and lower extreme (excluding outliers) (A and B). Rbc indicates red blood cell. Magnification 25000×; scale bars=1 μm (C and D). *P<0.05.

It is to be noted that the term "a" or "an" entity refers to one or more of that entity; for example, "an anti-Ang2 antibody" is understood to represent one or more anti-Ang2 antibodies. As such, the terms "a" (or "an"), "one or more," and "at least one" can be used interchangeably herein.

Angiopoietin-2

Many studies of Angiopoietin-2 ("Ang2" or "Ang-2") function have suggested a complex situation. Ang-2 might be a complex regulator of vascular remodeling that plays a role in both vessel sprouting and vessel regression. Supporting such roles for Ang-2, expression analyses reveal that Ang-2 is rapidly induced, together with VEGF, in adult settings of angiogenic sprouting, whereas Ang-2 is induced in the absence of VEGF in settings of vascular regression (Holash et al., Science 284:1994-98 (1999); Holash et al., Oncogene 18:5356-62 (1999)). Consistent with a context-dependent role, Ang-2 binds to the same endothelial-specific receptor, Tie-2, which is activated by Ang-1, but has context-dependent effects on its activation (Maisonpierre et al., Science 277:55-60 (1997)). In recent years Angiopoietin-1, Angiopoietin-2 and/or Tie-2 have been proposed as possible anti-cancer therapeutic targets (See, for example, U.S. Pat. Nos. 6,166,185, 5,650,490, 5,814,464, US Patent Publ. No. 20060018909 and Int. Publ. Nos. WO 2006/068953 and WO 2007/068895).

Angiogenesis is the process of forming new capillaries from preexisting blood vessels and is an essential component of embryogenesis, normal physiological growth, repair, and tumor expansion. Although a variety of factors can modulate endothelial cell (EC) responses in vitro and blood vessel growth in vivo, only vascular endothelial growth factor (VEGF) family members and the angiopoietins are believed to act almost exclusively on vascular ECs (Yancopoulos et al., Nature 407:242-48 (2000)).

The endothelium destabilizing properties of Ang-2 include induction of vascular leakage by promoting EC apoptosis and by disrupting EC-EC junctions (26). Ang-2 mediates endothelial dysfunction in various tissue stress conditions, such as airway inflammation, sepsis, hypoxia and in experimental ischemic heart and brain models (20, 27, 28). However, exogenous and endogenous Ang-2 have different effects (29), and their role in IRI is not fully understood. The IRI in an allograft is followed by early infiltration of innate immune inflammatory cells, mainly macrophages and neutrophils (30, 31). Cellular adhesion molecules play essential role in recruiting inflammatory cells to the site of injury. Ang1 inhibits leukocyte recruitment after LPS-induced endotoxicity and by preventing VEGF-induced endothelial adhesion molecule expression (32,33). In an acute kidney injury model, Kim et al. describe decrease of the ICAM-1 and VCAM-1 expression after therapy with a cartilage oligomeric matrix protein-Ang1 fusion (9). Ang-2 inhibition has been shown to decreases immunoreactivity of adhesion molecules in an ischemic mouse hind limb model (29). Furthermore, in a recent study with Ang2-overexpressing endothelial cells, Scholz et al. showed that Ang-2 has the capability of inducing inflammation and myeloid cell activation per se (1).

Antibodies

Embodiments described herein relate to methods of treatment using antibodies or antigen-binding fragments thereof specific for Ang-2, e.g., antibodies which can be derived from the antibody 3.19.3 (see, e.g., Int. Publ. No. WO 2009/097325) and which exhibit enhanced stability and/or production efficiencies, e.g., "MEDI1/5." In one embodiment the methods of the invention are directed to use of an antibody or antigen-binding fragment thereof comprising the six CDRs of anti-Ang2 antibody 3.19.3. The variable heavy and variable light chain amino acid sequences for anti-Ang2 antibody 3.19.3 are shown below.

```
3.19.3 light chain (SEQ ID NO: 1):
EIVLTQSPGTLSLSPGERATLSCRASQSITGSYLAWYQQKPGQAPRLLI

CGASSWATGIPDRFSGSGSGTDFTLTISRLEPEDFAVYYCQQYSSSPITF

GQGTRLEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC
```

The double underlined sequences represent VL CDRs 1-3, respectively. The underlined/bold residue in the 3.19.3 light chain sequence represents an unpaired cysteine (C49) that can be changed to any other amino acid. Examples of such changes are described in Int. Publ. No. WO 2009/097325.

```
3.19.3 heavy chain (SEQ ID NO: 2):
QVQLVESGGGVVQPGRSLRLSCAASGFTFTNYGMHWGRQAPGKGLEWVA
VISHDGNNKYYVDSVKGRFTISRDNSKNTLYLQMNSLRAEDTAVYYCAR
EGIDFWSGLNWFDPWGQGTLVTVSS
```

The double underlined sequences represent VH CDRs 1-3, respectively. The underlined/bold residue in the 3.19.3 heavy chain sequence represents an example of a residue that can be "backmutated" to another residue. One example of such a "backmutation" is represented in the "MEDI5" heavy chain sequence disclosed in Int. Publ. No. WO 2009/097325.

In some embodiments, the antibodies or antigen-binding fragments thereof bind to endogenous Ang-2 and inhibit the binding of Ang-2 to its receptor, Tie2. Other embodiments disclosed herein include fully human anti-Ang2 antibodies or antigen-binding fragments thereof, and antibody preparations that are therapeutically useful. Such anti-Ang2 antibody preparations have desirable therapeutic properties, including strong binding affinity for Ang-2, the ability to neutralize Ang-2 in vitro, and the ability to inhibit ischemia in Ang-2-expressing cells in vivo. In certain embodiments, the antibodies or antigen-binding fragments thereof disclosed herein comprise the ability to specifically bind Ang-2 and inhibit ischemia and/or reduce tissue inflammation. Mechanisms by which this can be achieved can include, but are not limited to, inhibition of binding of Ang-2 to its receptor Tie2, inhibition of Ang-2 induced Tie2 signaling, or increased clearance of Ang-2, therein reducing the effective concentration of Ang-2.

In certain embodiments, an anti-Ang2 antibody or antigen-binding fragment thereof for use in the methods described herein is derived from an anti-Ang2 antibody which is described in Int. Appl. No. WO 2009/097325, WO 2007/068895, or WO 2006/068953, each of which are incorporated herein by reference in their entireties. In one embodiment, the anti-Ang2 antibody or antigen-binding fragment thereof for use in the methods described herein is derived from anti-Ang2 antibody 3.19.3, e.g., MEDI1/5.

One aspect of the disclosure is directed to stabilized anti-Ang2 antibodies or antigen-binding fragments thereof for use in the methods described herein which comprise a substitution of an amino acid at position 49 (as compared to the light chain variable amino acid sequence of Ang-2 antibody 3.19.3, see SEQ ID NO: 1) as defined by the Kabat numbering system (Kabat et al., Sequences of Proteins of Immunological Interest, Fifth Edition, NIH Publication 91-3242, Bethesda Md. (1991), vols. 1-3). In one embodiment, the amino acid substitution at position 49 can be any amino acid. In a specific embodiment, the amino acid substitution at position 49 is selected from the group consisting of Asp, Thr, Asn, and Ala.

In another embodiment, the antibodies or antigen-binding fragments thereof for use in the methods described herein further comprises a Val substitution at position 37 of the heavy chain (as compared to the heavy chain variable amino acid sequence of Ang-2 antibody 3.19.3, see, SEQ ID NO: 2) as defined by the EU numbering system (Kabat et al., Sequences of Proteins of Immunological Interest, Fifth Edition, NIH Publication 91-3242, Bethesda Md. (1991), vols. 1-3).

In one embodiment, the antibodies or antigen-binding fragments thereof for use in the methods described herein exhibit enhanced stability as compared to antibody 3.19.3. In another embodiment, the antibodies or antigen-binding fragments thereof disclosed herein exhibit enhanced production yields as compared to 3.19.3.

In another embodiment, the antibodies or antigen-binding fragments thereof disclosed herein can comprise a variable light chain amino acid sequence selected from the group consisting of MEDI1 (SEQ ID NO: 3), MEDI2 (SEQ ID NO: 4), MEDI3 (SEQ ID NO: 5), MEDI6 (SEQ ID NO: 8), and MEDI4 (SEQ ID NO: 6). In another embodiment, the antibodies or antigen-binding fragments thereof disclosed herein can comprise the heavy chain variable amino acid sequence of MEDI5 (SEQ ID NO: 7). In another embodiment, the antibodies or antigen-binding fragments thereof disclosed herein can comprise variable light chain sequences selected from the group consisting of MEDI1 (SEQ ID NO: 3), MEDI2 (SEQ ID NO: 4), MEDI3 (SEQ ID NO: 5), MEDI6 (SEQ ID NO: 8), and MEDI4 (SEQ ID NO: 6) and further comprise the heavy chain variable sequence of MEDI5 (SEQ ID NO: 7).

In another embodiment, the antibodies or antigen-binding fragments thereof for use in the methods described herein can comprise variable light chain acid sequences selected from the group consisting of MEDI1 (SEQ ID NO: 3), MEDI2 (SEQ ID NO: 4), MEDI3 (SEQ ID NO: 5), MEDI6 (SEQ ID NO: 8), and MEDI4 (SEQ ID NO: 6), but having a different amino acid substitution at position 49. In another embodiment, the antibodies or antigen-binding fragments thereof disclosed herein can further comprise the heavy chain variable sequence of MEDI5 (SEQ ID NO: 7). In another embodiment, the antibodies or antigen-binding fragments thereof disclosed herein can comprise variable light chain sequences selected from the group consisting of MEDI1 (SEQ ID NO: 3), MEDI2 (SEQ ID NO: 4), MEDI3 (SEQ ID NO: 5), MEDI6 (SEQ ID NO: 8), and MEDI4 (SEQ ID NO: 6), but having a different amino acid substitution at position 49, and further comprise the heavy chain variable sequence of MEDI5 (SEQ ID NO: 7).

In some embodiments, antibodies or antigen-binding fragments thereof disclosed herein comprise a light chain which is engineered to remove at least one O-glycosylation site. In some embodiments, antibodies or antigen-binding fragments thereof disclosed herein comprise a light chain selected from the group consisting of MEDI1 (SEQ ID NO: 3), MEDI2 (SEQ ID NO: 4), MEDI3 (SEQ ID NO: 5), and MEDI4 (SEQ ID NO: 6) wherein the light chain further comprises an amino acid substitution at Kabat position 59, wherein the amino acid is not proline. In a specific embodiment, antibodies or antigen-binding fragments thereof disclosed herein comprise a light chain having the sequence corresponding to MEDI6 (SEQ ID NO: 8).

The variable light chain amino acid sequences MEDI1, MEDI2, MEDI3, MEDI4, and MEDI6; and the variable heavy chain amino acid sequence for MEDI5 are shown below. The double underlined sequences represent the VL and VH CDRs. The underlined residue is an example of a residue that can be "backmutated" to another residue.

```
MEDI1 light chain
                                       (SEQ ID NO: 3)
EIVLTQSPGTLSLSPGERATLSCRASQSITGSYLAWYQQKPGQAPRLLIT

GASSWATGIPDRFSGSGSGTDFTLTISRLEPEDFAVYYCQQYSSSPITF

GQGTRLEIKRTVAAPSVFIFPPSDEQLKSGTASVVCLLNNFYPREAKV

QWKVDNALQSGNSQESVTEQDSKDSTYSLSSTLTLSKADYEKHKVYAC

EVTHQGLSSPVTKSFNRGEC

MEDI2 light chain
                                       (SEQ ID NO: 4)
EIVLTQSPGTLSLSPGERATLSCRASQSITGSYLAWYQQKPGQAPRLLIN

GASSWATGIPDRFSGSGSGTDFTLTISRLEPEDFAVYYCQQYSSSPITF

GQGTRLEIKRTVAAPSVFIFPPSDEQLKSGTASVVCLLNNFYPREAKV

QWKVDNALQSGNSQESVTEQDSKDSTYSLSSTLTLSKADYEKHKVYAC

EVTHQGLSSPVTKSFNRGEC

MEDI3 light chain
                                       (SEQ ID NO: 5)
EIVLTQSPGTLSLSPGERATLSCRASQSITGSYLAWYQQKPGQAPRLLID

GASSWATGIPDRFSGSGSGTDFTLTISRLEPEDFAVYYCQQYSSSPITF

GQGTRLEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC

MEDI4 light chain
                                       (SEQ ID NO: 6)
EIVLTQSPGTLSLSPGERATLSCRASQSITGSYLAWYQQKPGQAPRLLIA

GASSWATGIPDRFSGSGSGTDFTLTISRLEPEDFAVYYCQQYSSSPITF

GQGTRLEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC

MEDI6 light chain
                                       (SEQ ID NO: 8)
EIVLTQSPGTLSLSPGERATLSCRASQSITGSYLAWYQQKPGQAPRLLIT

GASSWATGIADRFSGSGSGTDFTLTISRLEPEDFAVYYCQQYSSSPITF

GQGTRLEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC

MEDI5 heavy chain
                                       (SEQ ID NO: 7)
QVQLVESGGGVVQPGRSLRLSCAASGFTFTNYGMHWVRQAPGKGLEWVA

VISHDGNNKYYVDSVKGRFTISRDNSKNTLYLQMNSLRAEDTAVYYCAR

EGIDFWSGLNWFDPWGQGTLVTVSS
```

In certain embodiments, the methods disclosed herein are for use with an antibody comprising the three variable light chain (VL) CDRs of MEDI1 (SEQ ID NO: 3), MEDI2 (SEQ ID NO: 4), MEDI3 (SEQ ID NO: 5), MEDI4 (SEQ ID NO: 6), or MEDI6 (SEQ ID NO: 8) and the three variable heavy chain (VH) CDRs of MEDI5 (SEQ ID NO: 7). In certain embodiments, the methods disclosed herein are for use with an antibody comprising the VL sequence of MEDI1 (SEQ ID NO: 3), MEDI2 (SEQ ID NO: 4), MEDI3 (SEQ ID NO: 5), MEDI4 (SEQ ID NO: 6), or MEDI6 (SEQ ID NO: 8) and the VH sequence of MEDI5 (SEQ ID NO: 7). In some embodiments, the antibody of the methods disclosed herein is MEDI1/5, MEDI2/5, MEDI3/5, MEDI6/5, or MEDI4/5.

In one embodiment the anti-Ang2 antibody or antigen-binding fragment thereof is an antagonist of the biological activity of Angiopoietin-2. In further embodiments, the antagonist of Angiopoietin-2 is a monoclonal antibody. In yet further embodiments, the antagonist of Angiopoietin-2 is a fully human monoclonal antibody. In some embodiments the fully human monoclonal antibody is selected from any one of: 3.31.2, 5.16.3, 5.86.1, 5.88.3, 3.3.2, 5.103.1, 5.101.1, 3.19.3, 5.28.1, 5.78.3, MEDI1/5, MEDI2/5, MEDI3/5, MEDI6/5, or MEDI4/5, which are disclosed in Int. Publ. No. WO 2009/097325. In some embodiments the anti-Ang2 antibody disclosed herein comprises the six CDRs of an antibody selected from any one of: 3.31.2, 5.16.3, 5.86.1, 5.88.3, 3.3.2, 5.103.1, 5.101.1, 3.19.3, 5.28.1, 5.78.3, MEDI1/5, MEDI2/5, MEDI3/5, MEDI6/5, or MEDI4/5. In further embodiments, the fully human monoclonal antibody binds to the same epitope as any one of the following fully human monoclonal antibodies: 3.31.2, 5.16.3, 5.86.1, 5.88.3, 3.3.2, 5.103.1, 5.101.1, 3.19.3, 5.28.1, or 5.78.3, which are disclosed in Int. Appl. No. WO 2006/068953. In another aspect, the antibody of any of the methods disclosed herein binds to the same epitope as any one or more of the following antibodies: the MEDI1/5, MEDI2/5, MEDI3/5, MEDI6/5, or MEDI4/5.

The invention also provides antibodies that competitively inhibit binding of an antibody to a Ang-2 epitope as determined by any method known in the art for determining competitive binding, for example, the immunoassays and antibody binding assays described herein. In certain aspects, the antibody competitively inhibits binding to the epitope by at least 95%, at least 90%, at least 85%, at least 80%, at least 75%, at least 70%, at least 60%, or at least 50%. In certain aspects, the antibody of the invention competitively inhibits binding of MEDI1/5, MEDI2/5, MEDI3/5, MEDI6/5, or MEDI4/5 to Ang-2.

Methods of Treatment Using Anti-Ang2 Antibodies

Terms such as "treating" or "treatment" or "to treat" or "ameliorating" or "alleviating" or "to alleviate" can refer to both 1) therapeutic measures that cure, slow down, lessen symptoms of, reverse, and/or halt progression of a diagnosed pathologic disease, condition or disorder in a subject or tissue in vivo or ex vivo; and 2) prophylactic or preventative measures that prevent, reduce the risk of, and/or slow the development of a targeted pathologic disease, condition or disorder in a subject or tissue in vivo or ex vivo. Thus, a subject or tissue in need of treatment can include a subject or tissue already diagnosed with the disease, condition or disorder; a subject or tissue prone to have the disease, condition or disorder; and a subject or tissue for which the disease, condition or disorder is to be prevented. Beneficial or desired clinical results include, but are not limited to, alleviation of symptoms, diminishment of extent of the disease, condition or disorder; stabilized (i.e., not worsening) state of the disease, condition or disorder; delay or slowing of the progression of the disease, condition or disorder; amelioration or palliation of the disease, condition or disorder, and remission (whether partial or total), whether detectable or undetectable. "Treatment" can also mean prolonging survival as compared to expected survival if not receiving treatment. A subject or tissue in need of treatment include a subject or tissue already diagnosed with the disease, condition or disorder as well as a subject or tissue prone to have the disease, condition or disorder; or a subject or tissue in which the disease, condition or disorder is to be prevented.

By "subject" or "individual" or "animal" or "patient" or "mammal," is meant any subject, particularly a mammalian subject, for whom diagnosis, prognosis, or therapy is desired. In one aspect, the subject is a human.

By "tissue," is meant any body tissue or organ, e.g., heart, kidney, brain, smooth muscle or intestine tissue, particularly from a mammalian subject, for which diagnosis, prognosis, or therapy is desired. In certain embodiments, the tissue is an ischemic tissue, i.e., the tissue has undergone a period of ischemia or lack of oxygen. In certain embodiments, the ischemic tissue disclosed herein is injured by surgery, for example, by coronary artery bypass grafting, correction of a congenital heart defect, replacement of a heart valve, or heart transplantation.

In one embodiment, the tissue is an allograft. As used herein "allograft" is a tissue (e.g., solid organ) graft from a donor of the same species as the recipient but not genetically identical. In another embodiment, the tissue is an autograft. As used here an "autograft" is a tissue (e.g., bone, skin or blood vessels) that is transplanted within the same person's body.

Aspects disclosed herein include methods of using anti-Ang2 antibodies or antigen-binding fragments thereof for treating diseases or conditions, e.g., IRI, in a subject or tissue. In certain embodiments, the methods disclosed herein include using anti-Ang2 antibodies or antigen-binding fragments for modifying Ang-2 levels or Ang-2-mediated activities in a subject or tissue. For example, anti-Ang2 antibodies or antigen-binding fragments thereof are useful for preventing or reducing Ang-2 mediated Tie2 signal transduction. The mechanism of action of this inhibition can include inhibition of Ang-2 from binding to the receptor Tie2; inhibition of Ang-2 induced Tie2 signaling; Ang-2 mediated phosphorylation of Tie-2; or enhanced clearance of Ang-2, thereby lowering the effective concentration of Ang-2 for binding to Tie-2. In one embodiment, the anti-Ang2 antibody or antigen-binding fragment thereof reduces expression of VEGF, TGFβ, or both (e.g., for treatment of diseases, disorders or conditions associated with inflammation, vascular leakage or fibrosis). In another embodiment, the anti-Ang2 antibodies or antigen-binding fragments thereof can act through reducing circulating Ang-2 levels. In one embodiment, anti-Ang2 antibodies or antigen-binding fragments thereof can inhibit Ang-2 function in an ischemic molecular signaling cascade. In yet another embodiment, anti-Ang2 antibodies or antigen-binding fragments thereof are useful for inhibiting an IRI-induced inflammatory response.

Diseases, disorders or conditions that are treatable with an anti-Ang2 antibody or antigen-binding fragment thereof disclosed herein (e.g., MEDI1/5), e.g., through one or more of the inhibition/reduction mechanisms disclosed herein, include, but are not limited to, ischemic reperfusion injury (IRI) of any organ or tissue or multiple organs, such as heart (e.g., acute coronary syndrome), kidney (e.g., acute kidney injury), intestine (e.g., intestitial ischemia and multiorgan failure), brain (e.g., stroke, see, e.g., Liu et al., JBC 284 (34):22680-22689 (2009)); any type of vascular stroke; trauma and resuscitation (e.g., multiorgan failure, acute kidney injury, intestinal injury); or circulatory arrest (e.g., hypoxic brain injury, multiorgan failure, acute kidney injury). In another embodiment, the disease, disorder or condition is ischemia and/or reperfusion associated with major surgery in which the target organ or tissue is ischemic before, during, or after surgery, such as cardiac surgery (e.g., acute heart failure after cardiopulmonary bypass); thoracic surgery (e.g., acute lung injury); peripheral vascular surgery (e.g., compartment syndrome of extremity); major vascular surgery (e.g., acute kidney injury); and solid organ transplantation (e.g., acute graft failure, early graft rejection). In another embodiment, the disease, disorder or condition is a fibrotic or hypoxic condition (e.g., pulmonary fibrosis or lung hypoxia). In another embodiment, the disease, disorder or condition is accelerated or allograft artheriosclerosis. In another embodiment, the disease, disorder or condition is resuscitation of a subject, e.g., where circulatory collapse is followed by vascular leakage, e.g., in the lungs. In one embodiment, the subject has acute respiratory distress syndrome (ARDS) (see, e.g., Parikh, et al., *PLOS Medicine* 3(3):356-370 (2006)). In another embodiment, the disease, disorder or condition is sepsis, posttraumatic shock or hypoxic shock. Further embodiments disclosed herein include treatment of solid organ allografts in warm blood perfusion systems. Further embodiments disclosed herein also include treatment or prevention of chronic rejection of transplanted tissue, e.g., cardiac allografts. In certain embodiments, the subject to be treated by the methods disclosed herein has increased circulating Ang-2. In certain embodiments, the methods of treatment disclosed herein can be preceded by a diagnostic test. In certain embodiments, the disease, disorder or condition disclosed herein is diagnosed by measuring Ang2 levels in the subject, e.g., by detecting circulating Ang2 with an anti-Ang2 antibody disclosed herein.

In the broadest sense, ischemic reperfusion injury or ischemia and reperfusion-elicited tissue injury ("IRI") is the tissue damage caused when blood supply returns to the tissue after a period of ischemia or lack of oxygen. The absence of oxygen and nutrients from blood during the ischemic period creates a condition in which the restoration of circulation results in inflammation and oxidative damage through the induction of oxidative stress. IRI contributes to morbidity and mortality in a wide range of pathologies, e.g., single organ ischemia and reperfusion (e.g., of the heart, kidney, intestine and brain); multiple-organ ischemia and reperfusion (e.g., due to trauma and resuscitation, circulatory arrest, sickle cell disease, and sleep apnea); ischemia and reperfusion during major surgery (e.g., cardiac surgery, thoracic surgery, peripheral vascular surgery and solid organ transplantation). See, e.g. Eltzschig and Eckle, *Nature Medicine* 17(11):1391-1401 (2011). In certain embodiments, the subject suffers from one or more of the pathologies disclosed herein.

In addition or further to the pre-clinical models disclosed in detail herein, the additional diseases or disorders can be tested using models accepted in the art, e.g., for myocardial ischemia/reperfusion (e.g., Shyu et al., Clinical Science 105:287-294 (2003)); accelerated or allograft artheriosclerosis (e.g., Libby et al., Circulation 107:1237-1239 (2003)) and Nykanen et al., Circulation 107:1308-1314 (2003)); pulmonary leakage and congestion or ischemic pulmonary fibrosis (e.g., Parikh, et al., *PLOS Medicine* 3(3):356-370 (2006)); skin Delayed Type Hypersensitivity (DTH) (e.g., Dhabhar F S, *Brain Behav Immun.* 16(6):785-98 (2002)); kidney ischemia and kidney transplantation (e.g., Jung Y, et al., *Am J Physiol Renal Physiol.* 297(4):F952-60 (2009) and Salahudeen A K, Am J. Physiol Renal Physiol 287:F181-F187 (2004)); and ischemic stroke (e.g., Engel et al., *J. Vis. Exp.* (47), e2423, DOI: 10.3791/2423 (2011)).

In certain embodiments, the IRI disclosed herein is due to tissue transplantation (e.g., transplantation of a solid organ such as heart, kidneys, liver, lungs, pancreas, or intestine). In other embodiments, the IRI is due to cardiothoracic, vascular or general surgery; myocardial infarction; ischemic stroke; acute kidney injury; trauma or resuscitation; circulatory arrest; collapsed lung; sickle cell disease or sleep apnea.

One aspect disclosed herein is directed to a method for treating an IRI-induced inflammatory response in a subject or tissue comprising administering a therapeutically effective amount of an anti-Ang2 antibody or antigen-binding fragment thereof for use in the methods described herein to the subject or tissue in need thereof.

IRI is associated with disruption of vascular endothelial integrity, EC damage and subsequent pathological remodeling leading to chronic rejection. In one embodiment, the anti-Ang2 antibody or antigen-binding fragment thereof is administered to a tissue, e.g., intracoronary administration to a heart, to treat or protect the tissue from IRI.

Chronic rejection of cardiac allograts manifests as fibroblast proliferation, collagen deposition and vascular occlusion throughout the allograft, generally described as cardiac allograft vasculopathy (CAV). CAV manifests as allograft dysfunction, diastolic insufficiency and leads inevitably to graft failure. Graft failure is the main limiting factor of cardiac transplantation patient's survival (35). After decades of research, the pathophysiology of chronic rejection still remains somewhat unknown. Scientists and clinicians agree that the role of Th1-type T-cell mediated sustained inflammation as the main driving force towards chronic rejection. Thus, current clinical immunosuppresive strategies inhibit acute and chronic rejection development with steroids and IL-2 signaling targeted calcineurin inhibitors, such as cyclosporin A and tacrolimus, antimetabolites, and corticosteroids (36). However, even with sufficient immunosuppression preventing episodes of acute rejection, the development of CAV is still a significant survival limiting factor of cardiac allograft recipients (1). Emerging evidence suggest crucial role of IRI and innate immune responses in the activation of adaptive immune responses (37). IRI of the allograft exposes endogenous DAMPs, that are recognized by TLRs on antigen presenting cells, such as macrophages and DCs, resulting in DC maturation and migration to secondary lymphatic organs, where antigens are presented to naïve Th1-type T-cells (22). In addition, early microvascular dysfunction of cardiac, lung and renal allografts inflicts primary graft dysfunction and predicts the development of subsequent pathological changes (2. Hollenberg S M et al. Circulation. 2001; 104(25):3091-3096; Luckraz H et al. J Heart Lung Transplant. 2004; 23(5):527-531; Ishii Y et al. Transplant Proc. 2005; 37(2):981-983).

Another aspect is directed to a method for treating an IRI-induced microvascular dysfunction, cardiac fibrosis and/or chronic allograft vasculopathy (CAV) in a subject or tissue comprising administering a therapeutically effective amount of an anti-Ang2 antibody or antigen-binding fragment thereof described herein to the subject or tissue in need thereof. In certain embodiments, the anti-Ang2 antibody or antigen-binding fragment thereof is used for primary allograft protection. In certain embodiments, the anti-Ang2 antibody or antigen-binding fragment thereof is used in a perfusion solution for maintaining the endothelial integrity of the coronaries during the transplantation surgery.

In certain methods, the anti-Ang2 antibody or antigen-binding fragment thereof for use in the methods described herein are used to treat diseases associated with an inflammatory response.

Also disclosed herein are methods for reducing microvascular permeability in a tissue, increasing microvascular perfusion in a tissue, and/or reducing inflammation in a tissue comprising administering a therapeutically effective amount of an anti-Ang2 antibody or antigen-binding fragment thereof to a tissue in need thereof.

In another aspect disclosed herein, the method is directed to treating or ameliorating myocardial ischemia, comprising administering a therapeutically effective amount of an anti-Ang2 antibody or antigen-binding fragment thereof to a subject in need thereof. Another aspect of the disclosure is a method of protecting a solid organ transplant tissue, comprising administering an effective amount of an anti-Ang2 antibody or antigen-binding fragment thereof to an allograft. In yet another aspect, the method is directed to treating or preventing chronic rejection, comprising administering a therapeutically effective amount of an anti-Ang2 antibody or antigen-binding fragment thereof to a patient in need thereof.

The compositions and methods disclosed herein can be used with one or more conventional therapies that are used to prevent, manage or treat any of the above diseases or disorders.

In one embodiment, the anti-Ang2 antibody or antigen-binding fragment thereof for use in the methods described herein is administered as a monotherapy. In another embodiment, the anti-Ang2 antibody or antigen-binding fragment thereof for use in the methods described herein is administered in combination with other therapies. In one embodiment, the anti-Ang2 antibody or antigen-binding fragment thereof for use in the methods described herein is coadministered with one or more additional (or second) agents at the same time or a different time. In one embodiment, the method or use disclosed herein can be coadministered with an anti-inflammatory agent and/or an immunosuppressive agent, e.g., steroids; a biologic agent (see, e.g., Bann and Gaston, *American Journal of Transplantation* 11:681-686 (2011)), e.g., Belatacept, a CD20 or CD19 targeting antibody (e.g., Rituximab), a TNF targeting agent; or a calcineurin inhibitor, such as cyclosporin, tacrolimus, mycophenolic acid, azathioprine, statins, anti-thymocyte globuline, everolimus, or sirolimus.

Such conjoint or coadministered treatments can be achieved by way of the simultaneous, sequential or separate dosing of the individual components of the treatment. Such combination therapies can employ the antibodies or antigen-binding fragments thereof for use in the methods disclosed herein within the dosage range described herein and the other pharmaceutically active agent within its approved dosage range.

In another aspect, the methods are directed to administration of a composition, for example, but not limited to, a pharmaceutical composition, containing one or more anti-Ang2 antibodies or antigen-binding fragments thereof for use in the methods described herein, formulated together with a pharmaceutically acceptable carrier.

The methods disclosed herein can be formulated according to well-known methods (see, e.g., Hardman, et al. (2001) Goodman and Gilman's The Pharmacological Basis of Therapeutics, McGraw-Hill, New York, N.Y.; Gennaro (2000) Remington: The Science and Practice of Pharmacy, Lippincott, Williams, and Wilkins, New York, N.Y.; Avis, et al. (eds.) (1993) Pharmaceutical Dosage Forms: Parenteral Medications, Marcel Dekker, NY; Lieberman, et al. (eds.) (1990) Pharmaceutical Dosage Forms: Tablets, Marcel Dekker, NY; Lieberman, et al. (eds.) (1990) Pharmaceutical Dosage Forms: Disperse Systems, Marcel Dekker, NY; Weiner and Kotkoskie (2000) Excipient Toxicity and Safety, Marcel Dekker, Inc., New York, N.Y.).

By "therapeutically effective dose or amount" or "effective amount" is intended an amount of an anti-Ang2 antibody or antigen-binding fragment thereof for use in the methods described herein that when administered brings about a positive therapeutic response with respect to treatment of a subject or a tissue with the disease, condition or disorder to be treated.

Determination of the appropriate dose can be made by the clinician, e.g., using parameters or factors known or suspected in the art to affect treatment or predicted to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced.

Compositions comprising anti-Ang2 antibody or antigen-binding fragment thereof for use in the methods described herein can be provided as a single dose to a tissue (e.g., by perfusion) or subject (e.g., by continuous infusion or doses at intervals of, e.g., once daily, once weekly, or 1-7 times per week). Doses can be provided intracoronarily to a tissue, e.g., by perfusion to an allograft. A specific dose protocol is one involving the maximal dose or dose frequency that avoids significant undesirable side effects and can be determined by a person of ordinary skill in the art.

A total single, daily or weekly dose can be at least 0.05 ng/kg to at least 50 mg/kg (see, e.g., Yang, et al. (2003) New Engl. J. Med. 349:427-434; Herold, et al. (2002) New Engl. J. Med. 346:1692-1698; Liu, et al. (1999) J. Neural. Neurosurg. Psych. 67:451-456; Portielji, et al. (2003) Cancer Immunol. Immunother. 52:133-144). The single, daily or weekly dose can be at least 15 μg to 100 μg. The doses administered to a subject or tissue can number at least 1, 2, 3, 4, 5, 6, 7, 8, 9, 10, 11, or 12, or more.

The dosage of the anti-Ang2 antibody or antigen-binding fragment thereof for use in the methods described herein that is administered to a subject can be 0.0001 mg/kg to 100 mg/kg of the patient's body weight. The dosage of the anti-Ang2 antibody or antigen-binding fragment thereof for use in the methods described herein can be calculated using the subject's weight in kilograms (kg) multiplied by the dose to be administered in mg/kg. The dosage of anti-Ang2 antibody or antigen-binding fragment thereof for use in the methods described herein can be 150 μg/kg or less, 50 μg/kg or less, 25 μg/kg or less, 10 μg/kg or less, 5 μg/kg or less, 1 μg/kg or less, 0.5 μg/kg or less, or 0.5 μg/kg or less of a patient's body weight.

Unit dose of the anti-Ang2 antibody or antigen-binding fragment thereof for use in the methods described herein can be 0.1 mg to 20 mg.

The dosage of the anti-Ang2 antibody or antigen-binding fragment thereof for use in the methods described herein can achieve a serum titer of at least 0.1 μg/ml in a subject. Alternatively, the dosage of the anti-Ang2 antibody or antigen-binding fragment thereof for use in the methods described herein can achieve a serum titer of at least 0.1 μg/ml in the subject.

An effective amount for a particular subject or tissue can vary depending on factors such as the condition being treated, the overall health of the subject, the method route and dose of administration and the severity of side effects (see, e.g., Maynard, et al. (1996) A Handbook of SOPs for Good Clinical Practice, Interpharm Press, Boca Raton, Fla.; Dent (2001) Good Laboratory and Good Clinical Practice, Urch Publ., London, UK).

In certain embodiments, an allograft is perfused with an anti-Ang2 antibody or antigen-binding fragment thereof for use in the methods described herein. In one embodiment, the anti-Ang2 antibody or antigen-binding fragment thereof for use in the methods described herein is administered preoperatively. In some embodiments, the administration of an anti-Ang2 antibody or antigen-binding fragment thereof is prior to the removal of a graft from the donor (e.g., to the donor or donor tissue), prior to the transplantation of the graft to the recipient (e.g., to the donor tissue after removal from the donor, e.g., by perfusion of the organ), at the time of tissue reperfusion, after transplantation to the recipient (e.g., after reperfusion), or any combination thereof.

Another embodiment disclosed herein includes an assay kit for treating any of the diseases or disorders disclosed herein comprising an anti-Ang2 antibody or antigen-binding fragment thereof for use in the methods described herein.

Incorporation By Reference

All references cited herein, including patents, patent applications, papers, text books, and the like, and the references cited therein, to the extent that they are not already, are hereby incorporated herein by reference in their entirety.

EXAMPLES

I. Materials and Methods

Cell Cultures.

To analyze the effects of anti-Ang2 antibodies in hypoxic endothelial cells, human dermal blood microvascular endothelial cells (BECs) (PromoCell, Heidelberg, Germany) were maintained on fibronectin-coated dishes in Endothelial Cell Basal Medium MV (ECBM, PromoCell) with growth supplements provided by the manufacturer and used in passages 2-6. Hypoxic treatment (1% O2) was carried out in an Invivo2 400 hypoxia chamber (Ruskinn Technology, Bridgend, UK). Tie2-GFP retroviral transfected cells were produced as described in (Augustin et al., Nat Rev Mol Cell Biol. 2009; 10:165-177). Cells were treated with non-specific IgG (2 µg/ml) or anti-Ang2 andibodies (MEDI1/5) (2 µg/ml). The cells were fixed, permeabilized and stained for Ang2 and Tie2.

Transmission Electron Microscopy (TEM).

The effects of preservation prior to the transplantation were analyzed by recovering naïve Dark Agouti (DA, RT1av1) rat hearts and perfusing the coronaries with 200 µl of anti-Ang2 antibody (MEDI1/5; 150 ng/ml, in PBS) or non-specific IgG (150 ng/ml, in PBS). Next, the hearts were subjected to 4-h cold preservation, following 1-h warm preservation in room temperature. The samples of the the mid-cardiac specimens were collected and fixed with 2.5% glutaraldehyde in phosphate buffer (pH 7.4). The Advanced Microscopy Unit (Haartman Institute, University of Helsinki, Helsinki, Finland) prepared the samples by TEM-routine: samples were post-fixed in 1% osmium tetroxide, then dehydrated in graded ethanol, and embedded in Epoxy resin LX-112. Ultra-thin sections were cut at around 80 nm. Electron staining was performed with uranyl acetate and lead citrate in Leica EM STAIN automatic stainer. The sections were examined with JEM-1400 TEM (JEOL, Tokyo, Japan) at 80 KV and the incidence of endothelial cell (EC)-EC junction gaps and EC blebbing were analyzed with 25000× magnification.

Animals and Cardiac Allograft Models.

Heterotopic cardiac transplantations between fully MHC-mismatched pathogen-free inbred 8- to 12-week-old male Dark Agouti (DA, RT1av1) donor and Wistar Furth (WF, RT1u) recipient rats (Harlan Laboratories, Boxmeer, The Netherlands) were performed. Donor hearts were perfused with ice-cold heparinized phosphate-buffered saline (PBS) and then excised. For the ex vivo intracoronary treatment, the coronaries were then perfused with 200 µl of anti-Ang2 antibody (MEDI1/5; 150 ng/ml, in PBS), non-specific IgG (150 ng/ml, in PBS), or recombinant Ang2 (23) (50 µg/ml, in PBS). Unless stated otherwise, the allografts were subjected to 2 to 4-h hypothermic preservation before transplantation (i.e., the allografts were preserved in +4° C. PBS (cold ischemia) instead of immediate transplantation). Warm ischemia was standardized to 1 h. In the recipient treatment groups, the recipients received anti-Ang2 antibody (1 mg/kg, in PBS), or non-specific IgG (1 mg/kg, in PBS) i.p. 4 h before heart transplantation. Another group also received consecutive doses of anti-Ang2 antibody 1, 3, and 5 d after the transplantation.

The effect of cold preservation on the integrity of endothelial cells was analyzed by transmission electron microscopy in the non-transplanted donor hearts after 4-h cold and 1-h warm ischemia. After preservation, heterotopic cardiac transplantations were performed between fully MHC-mismatched, pathogen-free, inbred 8- to 12-week-old male DA donor and Wistar Furth (WF, RT1u) recipient rats (Harlan Laboratories, Boxmeer, The Netherlands) (Ono K and Lindsey E S., J Thorac Cardiovasc Surg. 1969; 57:225-229). After reperfusion, the recipients were sacrificed at 30 min to analyze the effect on microvascular perfusion and permeability with lectin perfusion and modified Miles assay, at 6 h to analyze endothelial activation, inflammatory cell influx, myocardial injury, and innate immune activation, and at 8 weeks to analyze the activation of adaptive immune response and microvascular density and the degree of cardiac fibrosis and allograft vasculopathy. To prevent irreversible episodes of acute allograft rejection, to achieve long-term allograft survival, and to enable the development of chronic rejection, the recipients received s.c. cyclosporine A (Novartis, Basel, Switzerland) 2 mg/kg/day for the first 7 days and 1 mg/kg/day thereafter. All allografts were beating upon recovery. Each group included six to eight animals.

The State Provincial Office of Southern Finland approved all animal experiments. The animals received care in compliance with the Guide for the Care and Use of Laboratory Animals as outlined by the National Academy of Sciences (ISBN 0-309-05377, revised 1996). The rats inhaled isoflurane (Isofluran, Baxter, Deerfield, Ill.) in anesthesia and received buprenorphine (Temgesic, Schering-Plough, Kenilworth, N.J.) for perioperative analgesia.

Microvascular Leakage and Reflow.

A modified Miles Assay was used to measure extravasation of plasma proteins from the microvasculature into the interstitial space of cardiac allografts. Immediately after reperfusion, the recipients were injected (i.v.) with Evans Blue dye (Sigma-Aldrich; 30 mg/ml diluted in 0.9% NaCl; n=6 or 7), which circulated for 30 min. To detect perfused vessels 30 min after reperfusion, 50 µl FITC-labeled *Lycopersicon esculentum* (tomato) lectin (Vector Laboratories, Burlingame, Calif.) diluted in 150 µl of 0.9% NaCl was injected into the aortic root a few minutes before removing the allografts. Immediately thereafter, a small incision to the right ventricle was made and the coronary network was retrogradely flushed with 5 ml of 1% PFA in 0.05 M citrate buffer, pH 3.5. For quantification of extravasated Evans Blue, 100 mg of apical myocardium was dissolved into 500 µl of formamide and left on a shaker at +60° C. for 24 h. The absorbance of formamide containing dissolved Evans Blue dye was measured by spectrophotometry at 610 nm wavelength. FITC positive microvascular vessels were quantified from mid-axial cross sections from 10 random fields of each cardiac cross section by fluorescence microscopy, and the result was given as the mean density of perfused vessels per $mm^2$.

Acute Myocardial Injury.

Myocardial troponin T (TnT) levels in serum samples, derived at 6 h after reperfusion, were used to determined acute myocardial injury. TnT was analyzed with the fifth generation TnT test (Troponin T STAT, Roche Diagnostics, Mannheim, Germany), which showed cross-reactivity of 0.001% with TnT originating in skeletal muscle at a concentration of 2.000 ng/ml. The functional sensitivity was 0.05 µg/l and the lower detection limit 0.01 µg/l. The TnT was measured by electrochemiluminescence immunoassay (ECLIA) with the Elecsys 2010 immunoassay analyzer (Roche Diagnostics).

RNA Isolation and Quantitative RT-PCR.

Total RNA was isolated from tissue samples dissected from the myocardial midpiece of the allografts according to the manufacturer's instructions using RNeasy kit (Qiagen, Hilden, Germany) and reverse transcribed with the High-RNA-to-cDNA kit (Applied Biosystems, Foster City, Calif.). Quantitative real-time PCR (RT-PCR) was performed on a RotorGene-6000 (Corbett Research, Doncaster, Australia) using 2× DyNAmo Flash SYBR Green Master mix (Finnzymes, Espoo, Finland). The mRNA quantities of the following factors were measured from each group: innate immune receptors TLR2 and TLR4, their ligands biglycan, HAS1-3, HMGB1, transcription factor NF-κB, dendritic cell (DC) maturation markers CD80, CD86, and CD83, inflammatory cytokines TNF-α, IL-1β, IP-10, TGF-β, IL-6 and IL-10. The number of mRNA copies of the gene of interest was calculated from a corresponding standard curve using RotorGene software. Of tested housekeeping genes (18SRNA, GAPDH, β-actin and TBP), 18SRNA was most stably expressed and therefore all RT-PCR data were normalized against 18SRNA. Primers are shown in Table 1.

TABLE 1

The genes and corresponding GenBank access numbers for the primers used in the RT-PCR analysis.

| Gene Name | GenBank No. |
|---|---|
| HAS1 | NM_172323 |
| HAS2 | NM_013153 |
| HAS3 | NM_172319 |
| Biglycan | NM_017087 |
| HMGB1 | NM_012963 |
| TLR2 | NM_198769 |
| TLR4 | NM_019178 |
| NFκB | L26267 |
| IL1b | NM_031512 |
| IL2 | NM_053836 |
| IL4 | NM_201270 |
| IL6 | NM_012589 |
| IL10 | NM_012854 |
| IL12p35 | NM_053390 |
| TNFα | NM_012675 |
| IFNγ | NM_138880 |
| IP10 | RNU22520 |
| VEGF-A | NM_031836 |
| CD80 | NM_012926 |
| CD83 | NM_001108410 |
| CD86 | NM_020081 |
| TGFβ | NM_021578 |
| KLF2 | NM_001007684 |
| Ang1 | NM_053546 |
| Ang2 | NM_134454 |
| LFA-1 | NM_001037780 |
| VCAM-1 | NM_012889 |
| ICAM-1 | NM_012967 |
| 18SrRNA | X01117 |
| β-actin | NM_031144 |
| TBP | NM_001004198 |
| GAPDH | BC087743 |

Immunohistochemistry and Immunofluorecence Stainings.

Cryostat sections were stained for subsets of inflammatory cells and vessels using the peroxidase ABC method (Vectastain Elite ABC Kit, Vector Laboratories) and the reaction was developed with 3-amino-9-ethylcarbazole (AEC, Vectastain). Immunofluorescent staining was performed using Alexa 568 red and Alexa 488 green (Promega, Madison, Wis.) secondary antibodies. We used the following antibodies and dilutions: RECA-1 for endothelium (50 μg/ml, MCA97, AbD Serotec, Dusseldorf, Germany); CD4 for T cells (5 μg/ml, 22021D, BD Pharmingen, San Diego, Calif.), CD8 for T cells (5 μg/ml, 22071D BD Pharmingen), ED1 for macrophages (5 μg/ml, 22451D, BD Pharmingen); MPO for neutrophils (20 μg/ml, ab9535, Abcam, Cambridge, UK); OX62 for dendritic cells (10 μg/ml, MCA 1029G, Serotec, Oxford, UK); VCAM-1 (10 μg/ml, MMS-141P, Covance, Princeton, N.J.); p-adducin (phospho T445, 10 μg/ml, ab58485, Abcam). The immunoreactivity was quantified in a blinded manner using 200× or 400× magnification.

Enzyme-Linked Immunosorbent Assay (ELISA).

To quantify Ang2 from human and rat serum samples, ELISA was performed according to the Manufacturer's instructions: human Ang2 (DANG20; R&D Systems); rat Ang2 (E90009Ra; Uscn Life Science Inc., Wuhan, China).

Histology.

Paraformaldehyde-fixed paraffin mid-cardiac cross sections were used for histological staining. The degree of cardiac fibrosis was determined from cross sections stained with Masson's trichrome staining and scored using computer-assisted image processing (Zeiss Axiovision 4.4, Munich, Germany) by measuring the average proportional area stained for fibrosis from photographs captured with 100× magnification. Chronic allograft vasculopathy was determined from cross sections stained with hematoxylin-eosin and Resorcin-Fuchsin (for internal elastic lamina) by measuring the area between the internal elastic lamina and vessel lumen. Arterial occlusion percentage was determined as the ratio of neointimal area to internal elastic lamina area. Small (diameter<40 μm), medium (40-120 μm) and large arteries (>120 μm) were distinguished and analyzed separately.

Statistics.

All data are mean±SEM by box plots showing the upper extreme (excluding outliers), upper quartile, median, lower quartile, and lower extreme (excluding outliers) for continuous variables (SPSS Statistics 15.0; SPSS Inc., Somers, N.Y.). The outliers are shown as circles outside the box and analyzed by Mann-Whitney U test using PASW Statistics 19.0 (SPSS Inc., Chicago, Ill.). $P<0.05$ was considered to be statistically significant.

II. Results

Example 1. Hypoxia Increases Ang2 Deposition in Endothelial Cell-Cell Junctions and Ex Vivo Intracoronary Perfusion with Anti-Ang2 Antibody Promoted Endothelial Stability During Cold and Warm Ischemia In cultures of human umbilical vein endothelial cells, Ang2 expression and secretion is increased in response to hypoxia (15). In order to model Ang2 function in the allograft microvasculature, endothelial cell monolayers were subjected to hypoxia for various periods of time, and Ang2 was analyzed by immunoflorescent staining. The results demonstrated that a 16-24 h period of hypoxic culture induced deposition of Ang2 in EC-EC junctions where Ang2 co-localized with Tie2. Anti-Ang2 antibody (MEDI1/5), but not control-IgG, inhibited the deposition of Ang2-Tie2 complexes (FIG. 1). Ang2 competes with Ang1 for binding to Tie2 in endothelial cell junctions, but is a weaker agonist of Tie2 phosphorylation than Ang1 (Saharinen P, et al., Nat. Cell Biol. 2008; 10:527-537). Thus, these results support that endogenous Ang2 has inhibitory effects on Ang1 signaling, and that blocking endogenous Ang2 may be useful in treatment of conditions originating from ischemia/hypoxia.

The effect of Ang2 neutralization on endothelial integrity was also tested. Hypoxia induces EC blebbing—a phenomenon described by formation of cell membrane protrusions and disintegration—and promotes endothelial instability. Hypothermic (cold) and warm preservation induces EC-EC gap formation in a cardiac allograft model (38). Transmission electron microscopy (TEM) imagining of non-transplanted DA hearts subjected to 4-h hypothermic and 1-h warm preservation demonstrated that intracoronary perfusion with anti-Ang2 antibody (MEDI1/5) inhibited EC blebbing and EC-EC gap formation compared to abundant blebbing and EC-EC gap formation in the control-IgG-treated allografts (FIG. 2A-D; $P<0.05$). The results show that inhibition of Ang2 with neutralizing antibodies increases endothelial stability. Furthermore, these results support that Ang2 acted as an endothelium destabilizing Ang1 antagonist, in rat cardiac allografts, and supports that Ang2 destabilizes microvascular endothelium in the heart during preservation.

Example 2. Ex Vivo Intracoronary Perfusion with Anti-Ang2 Prevented Microvascular Permeability and No-Reflow Phenomenon During Reperfusion in Cardiac Allografts The inhibition of endogenous Ang2 signaling with Ang2 blocking antibody (MEDI1/5) was evaluated. Microvascular leakage was analyzed with a modified Miles assay and microvascular no-reflow phenomenon was analyzed with fluorecent lectin perfusion 30 min after reperfusion. Allografts were intracoronarily perfused with recombinant anti-Ang2 antibody (MEDI1/5) (n=8) or IgG control (n=7); subjected to a 4-h hypothermic preservation; and transplanted and recovered at 30 minutes after reperfusion (after transplantation, the clamps preventing bloodflow were opened and circulation to the allograft was re-established). As used herein, this perfusion of ischemic organ or tissue is called reperfusion. The allograft started beating within about a minute. Vascular permeability results were measured by quantifying Evans Blue absorbance from the myocardium at 30 minutes after reperfusion. Capillary perfusion results were measured by quantifying tomato lectin positive capillaries from cardiac cross sections from at least 10 random immunofluorecent images. The mean density of the capillaries was measured by quantifying lectin positive vessels in histological sections. Anti-Ang2 antibody treatment was compared to control allografts at 30 minutes after reperfusion. The Mann-Whitney U test was used to compare anti-Ang2 and IgG treatment.

Figure 3:
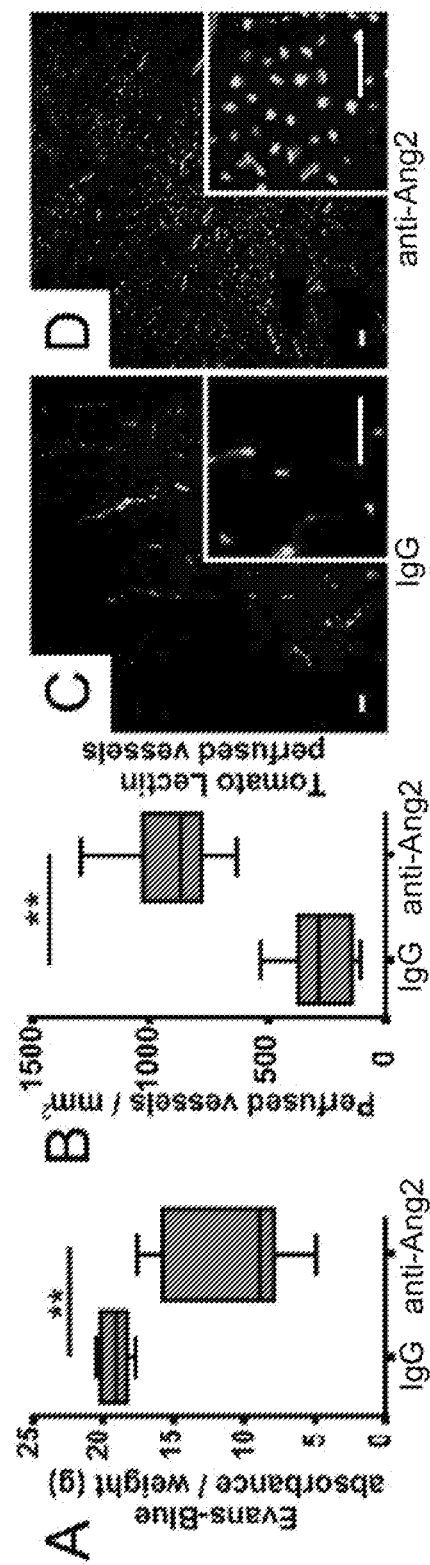
FIG. 3 shows that the anti-Ang2 antibody (MEDI1/5) reduces vascular endothelium permeability and increases the number of perfused capillaries after cardiac allograft IRI. (A) Shows vascular permeability results measured by quantifying Evans Blue absorbance from the myocardium at 30 minutes after reperfusion. Evans Blue from the myocardium treated with anti-Ang2 antibody is compared to control IgG at 30 min after reperfusion (p<0.05). (B) Shows capillary perfusion results measured by quantifying tomato lectin positive capillaries from cardiac cross sections from at least 10 random immunofluorecent images. The mean density of the capillaries was measured by quantifying *Lycopersicon esculentum* (tomato) lectin positive vessels in histological sections, anti-Ang2 antibody treatment compared to control allografts, at 30 min. **p<0.01, n=8 per group. (C-D) Show examples of control IgG and anti-Ang2 antibody tomato lectin positive capillaries from cardiac cross sections. Magnification 100×, inset 400× (Scale bar represents 20 μm). (E) Shows the tissue perfusion in the apical myocardium of cardiac allografts determined by Doppler velocimeter during the first 10 min after reperfusion. n=8 per group; repeated measurements ANOVA (E).
Figure 3:
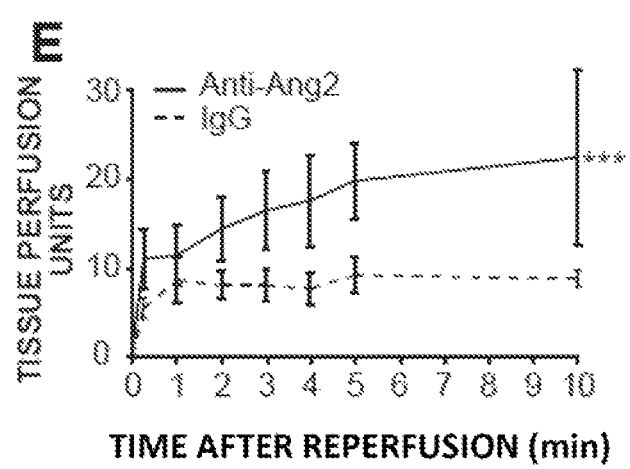

Preoperative intracoronary administration of anti-Ang2 antibody (MEDI1/5) significantly decreased the endothelial permeability measured by myocardial absorbance of extravasated Evans Blue dye, compared to IgG-control allografts at 30 min ($p<0.01$; FIG. 3A). Furthermore, anti-Ang2 perfused allografts had significantly increased microvascular perfusion ($P<0.01$; FIG. 3B-D).

Doppler velocimeter recording for DA donor rat hearts recovered and intracoronarily administered either anti-Ang2 antibody (MEDI1/5) or with control-IgG, subjected to 4-h cold ischemia and transplanted to fully MHC-mismatched WF recipient rats were analyzed. The results demonstrated that the tissue perfusion in the apical myocardium was significantly better in the anti-Ang2-treated allografts when compared to the IgG-treated allografts during the first 10 minutes of reperfusion (FIG. 3E).

These results show that treatment with a single dose of anti-Ang2 antibody to inhibit endogenous Ang2 reduced vascular permeability and increased the number of perfused myocardial capillaries immediately after reperfusion of the allograft compared to PBS-perfused allografts.

Figure 4:
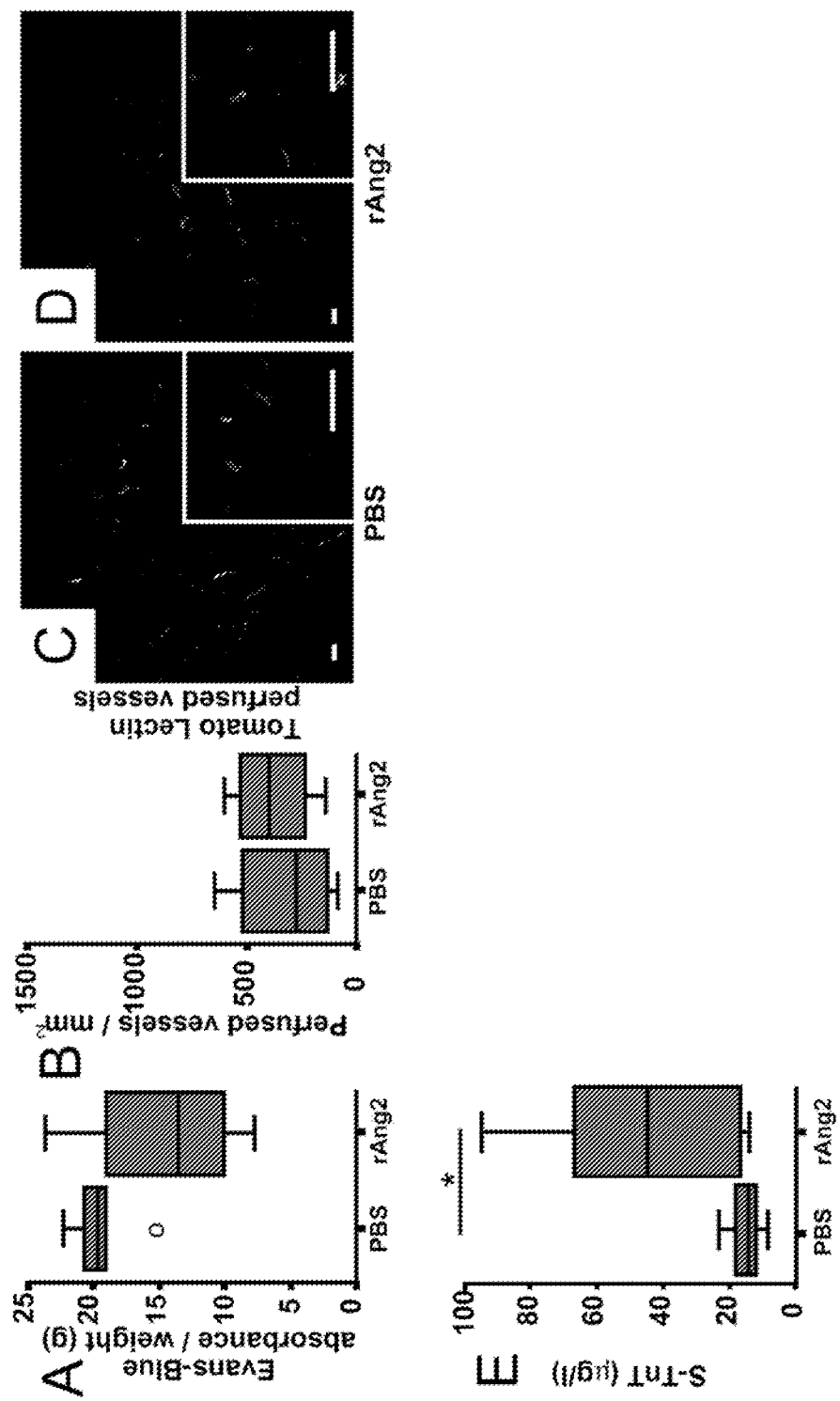
FIG. 4 shows intracoronary perfusion with recombinant Ang2 has no effect on microvascular dysfunction 30 min after reperfusion, but increases myocardial injury 6 h after reperfusion. (A) Shows vascular permeability measured by quantifying myocardial absorbance of extravasated Evans Blue dye with spectrofotometry at 610 nm 30 min after reperfusion. (B-D) Show myocardial capillary perfusion measured by quantifying the density of endothelium-binding FITC-conjugated *Lycopersicon esculentum* (tomato) lectin (green). (E) Shows the serum levels of cardiomyocyte specific troponin T (TnT). n=5 to 6 per group. The Mann-Whitney U test was used to compare recombinant (rAng2) and PBS treatment. Magnification 100×, inset 400× (Scale bars=20 μm). (F-J) Shows ex vivo intracoronary perfusion with exogenous recombinant Ang2 worsens allograft inflammation. The numbers of allograft-infiltrating ED1+ macrophages, MPO+ neutrophils, CD4+ T cells, CD8+ T cells, and OX62+ dendritic cells 6 h after reperfusion (n=6 per group). Data are given by box plots showing the upper extreme (excluding outliers), upper quartile, median, lower quartile, and lower extreme (excluding outliers). *P<0.05 using the Mann-Whitney U test (F-J).
Figure 4:
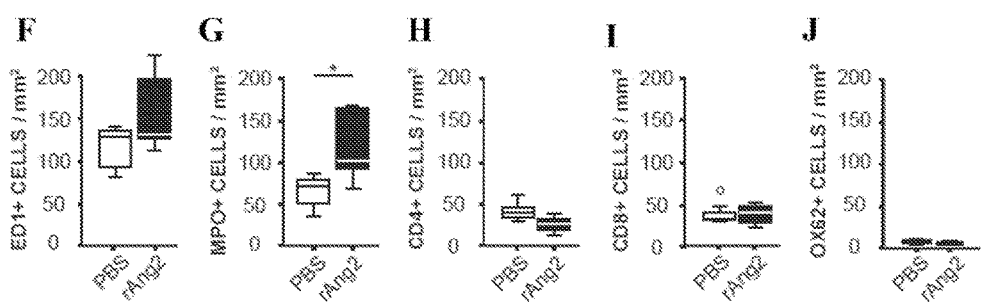

Example 3. Intracoronary Perfusion with Recombinant Ang2 Aggravates IRI-Induced Myocardial Damage The effect of exogenous, recombinant Ang2 on acute myocardial injury in rat cardiac allograft model was also analyzed. The allografts were intracoronarily perfused with recombinant Ang2 or control PBS and subjected to a 4-h hypothermic preservation, transplanted and recovered at 6-h after reperfusion. Vascular permeability was measured by quantifying myocardial absorbance of extravasated Evans Blue dye with spectrofotometry at 610 nm 30 min after reperfusion. Myocardial capillary perfusion was measured by quantifying the density of endothelium-binding FITC-conjugated *Lycopersicon esculentum* lectin. Vascular permeability and perfusion 30 min after reperfusion remained unchanged between the groups as shown in FIG. 4A-D. Six (6) h after reperfusion, intracoronary perfusion with rAng2 increased serum TnT. The serum levels of cardiomyocyte specific troponin T (TnT) (n=5 to 6 per group, $P<0.05$) is shown in FIG. 4E. These results show that ex vivo intracoronary perfusion with exogenous recombinant Ang2 in the rat IRI model had no effect on permeability and perfusion 30 min after reperfusion, but increased serum TnT levels, as a sign of extensive myocardial injury, 6 h after reperfusion compared to PBS. These results support that rAng2 is detrimental to the allograft.

Ex vivo intracoronary perfusion with exogenous recombinant Ang2 alone was shown to worsen allograft inflammation. The allograft-infiltrating ED1+ macrophages, MPO+ neutrophils, CD4+ T cells, CD8+ T cells, and OX62+ dendritic cells 6 h after reperfusion (n=6 per group) are shown in FIG. 4F-J. rAng2 significantly increased the numbers of allograft infiltrating ED1+ macrophages and MPO+ neutrophils 6 h after reperfusion (which correlated with greater myocardial injury in these groups). The ex vivo intracoronary treatment of allografts with recombinant Ang2 (rAng2) alone did not affect microvascular leakage or no-reflow phenomenon 30 min after reperfusion, but rAng2 treatment induced severe myocardial injury and increased inflammatory cell influx when compared to the PBS-treatment. These results show a pro-inflammatory role for Ang2 in IRI in cardiac allografts.

Example 4. Ex Vivo Intracoronary Perfusion with Anti-Ang2 Decreases IRI-Induced Myocardial Damage and Inflammation in Cardiac Allografts Cardiomyocytes are highly susceptible to ischemic injury (42). The effect of anti-Ang2 antibody (MEDI1/5) on IRI-triggered cardiac damage and on inflammatory responses in transplanted hearts was investigated.

Figure 5:
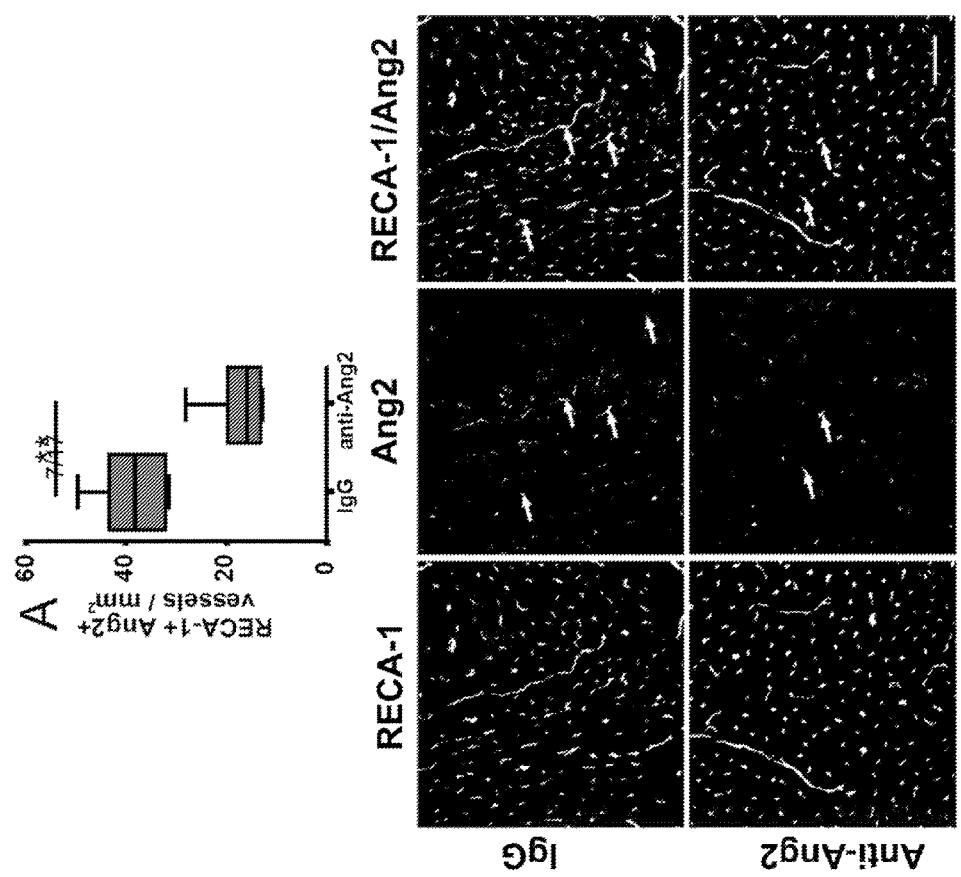
FIG. 5 shows intracoronary perfusion with anti-Ang2 reduced the immunoreactivity of Ang2 6 h after reperfusion. (A) Shows the expression of endothelial Ang2 measured by quantifying the density of Ang2/rat endothelial cell antigen (RECA-1) double positive vessels 6 h after transplantation (n=6 per group). (B) Shows myocardial Ang2 expression visualized by immunofluorecence staining for Ang2 and RECA-1. The Mann-Whitney U test was used to compare anti-Ang2 and IgG treatment. Data are given by box plots showing the upper extreme (excluding outliers), upper quartile, median, lower quartile, and lower extreme (excluding outliers). **P<0.01 (Scale bars=20 μm).

Expression of endothelial Ang2 was measured by quantifying the density of Ang2/rat endothelial cell antigen (RECA-1) double positive vessels 6 h after transplantation (n=6 per group) (FIG. 5A). Myocardial Ang2 expression was visualized by immunofluorecence staining for Ang2 and RECA-1 (FIG. 5B). The Mann-Whitney U test was used to compare anti-Ang2 and IgG treatment (Scale bars=20 μm). These results showed that intracoronary perfusion with anti-Ang2 reduced Ang2 expression in the endothelium of the allografts 6 hours after transplantation compared to IgG perfusion (P<0.01).

The allografts were intracoronarily perfused with anti-Ang2 antibody or control IgG and subjected to a 4-h hypothermic preservation, transplanted and recovered at 6-h after reperfusion. Serum levels of cardiomyocyte specific troponin T (TnT) was measured. In addition, intragraft ED1+ macrophages, MPO+ neutrophils, CD4+ and CD8+ lymphocytes and OX62+ DCs were measured. VCAM-1+ vessels were quantified from histological images of vessels from control IgG and anti-Ang2 antibody treated groups, respectively.

Figure 6:
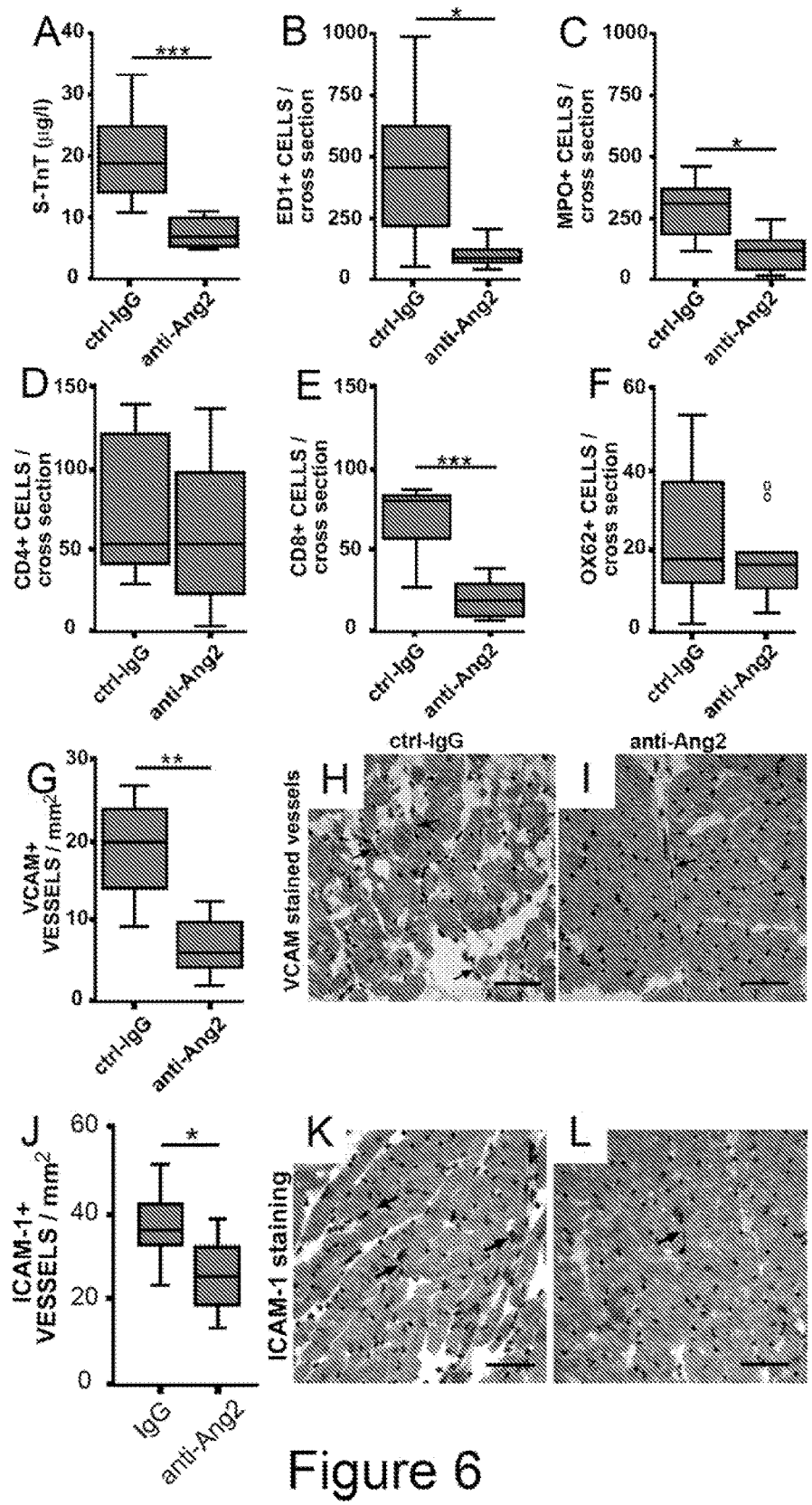
FIG. 6 shows that the anti-Ang2 antibody (MEDI1/5) decreases early myocardial damage, inflammatory cell influx, adhesion molecule expression and early innate immune activation. The allografts were intracoronarily perfused with anti-Ang2 antibody or control IgG and subjected to a 4-h hypothermic preservation, transplanted and recovered at 6 h after reperfusion. (A) Shows serum levels of cardiomyocyte specific troponin T (TnT). n=6-9 per group. (B-F) Show quantification of intragraft ED1+ macrophages, MPO+ neutrophils, CD4+ and CD8+ lymphocytes and OX62+ DCs, respectively. n=8-9 per group. (G and J) Shows quantification of VCAM-1+ and ICAM-1+ vessels, respectively, and (H-I and K-L) show representative histological images of VCAM-1+ and ICAM-1+ vessels from control IgG and anti-Ang2 antibody treated groups, respectively. n=8-9 per group. The Mann-Whitney U test was used to compare anti-Ang2 and IgG treatment. *p<0.05; p<0.01; *p<0.001. (Scale bar represents 20 μm).

Cardiomyocytes are highly susceptible to ischemic injury (Gottlieb R A. J Cardiovasc Pharmacol Ther. 2011; 16(3-4):233-238). The degree of allograft myocardial injury was assessed by analyzing serum TnT levels. The anti-Ang2 treatment significantly reduced IRI-induced serum TnT release compared to control IgG treatment at 6 h (p<0.001; FIG. 6A). Preliminary results showed that using 0.1-fold amount of anti-Ang2 antibody (MEDI1/5) did not reduce serum TnT levels, and that using 10-fold amount of anti-Ang2 antibody did not provide additional serum TnT release.

Endothelial activation was measured at 6 h after reperfusion, and ex vivo intracoronary perfusion with MEDI1/5 significantly reduced vascular cell adhesion molecule-1 (VCAM-1) and intracellular adhesion molecule-1 (ICAM-1) immunoreactivity in the microvasculature when compared to IgG treatment (P<0.01; FIG. 6G-L). The number of graft infiltrating ED1+ macrophages, MPO+ neutrophils and CD8+ lymphocytes were also significantly reduced in anti-Ang2 treated allografts compared to control IgG group at 6 h (FIGS. 6B-C and E). The anti-Ang2 antibody treatment had no significant effect on infiltrating CD4+ lymphocytes or OX62+ dendritic cells (FIGS. 6D and F).

IRI releases target tissue derived endogenous danger molecules. These danger/damage-associated molecular patterns ligate to Toll-like receptors (TLRs) and form a link between the innate immunity and the activation of the adaptive immunity that may ultimately be detrimental for an allograft. The mRNA expression levels of endogenous TLR-receptors and ligands 6 h after reperfusion with anti-Ang2 antibody was measured. Compared to IgG treatment, the anti-Ang2 antibody (MEDI1/5) treatment significantly decreased mRNAs encoding innate immune mediators HAS1-3 and NFkB, inflammatory cytokines IL-1β, IL-2 and IL-12p35 and transforming growth factor (TGF)β compared to PBS treatment (Table 2, P<0.05). VEGF increases vascular permeability by directly disrupting EC-EC tight junctions (43), but also by increasing Ang2 production (1). A significant decrease in VEGF mRNA expression in the anti-Ang2 antibody treated allografts at 6 h after reperfusion was observed compared to PBS treatment (Table 2, P<0.01).

TABLE 2

| Gene | Anti-Ang2/ctrl-PBS ± SEM | p |
|---|---|---|
| HAS1 | 0.50 ± 0.07 | 0.021* |
| HAS2 | 0.62 ± 0.10 | 0.028* |
| HAS3 | 0.25 ± 0.11 | 0.010** |
| Biglycan | 0.71 ± 0.17 | 0.105 |
| HMGB1 | 0.78 ± 0.14 | 0.161 |
| TLR2 | 0.54 ± 0.10 | 0.281 |
| TLR4 | 0.66 ± 0.08 | 0.779 |
| NFkB | 0.76 ± 0.08 | 0.029* |
| IL1b | 0.43 ± 0.05 | 0.040* |

TABLE 2-continued

| Gene | Anti-Ang2/ctrl-PBS ± SEM | p |
|---|---|---|
| IL2 | 0.56 ± 0.15 | 0.050* |
| IL4 | 0.70 ± 0.14 | 0.105 |
| IL6 | 0.40 ± 0.04 | 0.073 |
| IL10 | 0.63 ± 0.14 | 0.161 |
| IL12p35 | 0.54 ± 0.08 | 0.007** |
| TNFa | 0.35 ± 0.11 | 0.054 |
| IFNg | 0.74 ± 0.21 | 0.382 |
| IP10 | 0.77 ± 0.19 | 0.328 |
| VEGF-A | 0.61 ± 0.05 | 0.021* |
| CD80 | 0.66 ± 0.08 | 0.442 |
| CD83 | 0.86 ± 0.11 | 0.959 |
| CD86 | 0.81 ± 0.08 | 0.574 |
| TGFb | 0.77 ± 0.06 | 0.050* |
| KLF2 | 0.80 ± 0.07 | 1.000 |
| Ang1 | 0.78 ± 0.16 | 0.161 |
| Ang2 | 0.87 ± 0.15 | 0.721 |

These results show that the anti-Ang2 antibody treatment efficiently reduced the immunoreactivity of VCAM-1. Furthermore, these experiments showed that the anti-Ang2 antibody treatment significantly decreased the influx of not only graft infiltrating ED1+ macrophages and MPO+ neutrophils, but also CD8+ T cells 6 h after reperfusion.

A decrease in mRNA expression of innate immune activation markers in anti-Ang2 antibody treated allografts 6 h after reperfusion was also observed. Anti-Ang2 antibody treated allografts had significantly reduced mRNA expression of VEGF and profibrotic TGFβ.

These results show that anti-Ang2 antibody treatment decreases the activation of endothelium, accumulation of inflammatory cells, and subsequent acute myocardial injury and innate immune responses.

Figure 7:
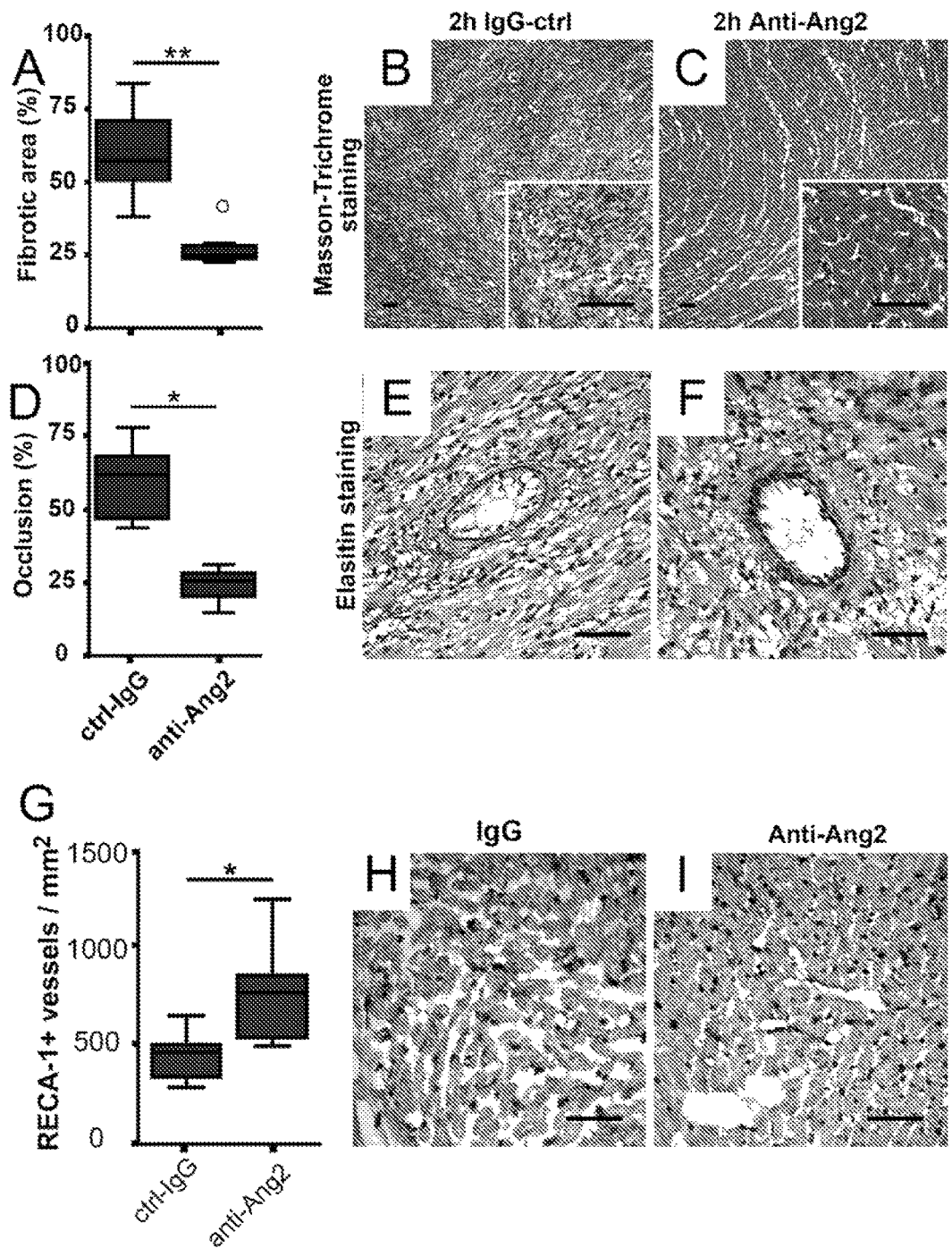
FIG. 7 shows that anti-Ang2 antibody (MEDI1/5) reduces cardiac fibrosis and cardiac allograft vasculopathy 8 weeks after transplantation. The allografts were intracoronarily perfused with the anti-Ang2 antibody or control IgG and subjected to a 2-h hypothermic preservation, transplanted and recovered at 8 weeks. (A) Shows the results for quantification of cardiac fibrosis assessed with Masson's trichrome staining for control IgG and anti-Ang2 antibody treated groups. Computer assisted analysis was performed to measure the area stained blue for fibrosis from at least 10 images. (B-C) Show examples of cardiac cross sections with Masson's trichrome staining for control IgG and anti-Ang2 antibody, respectively. (D) Shows the results for quantification of the degree of occlusion for control IgG and anti-Ang2 antibody treated groups. Data are indicated as mean±SEM, analyzed with Mann-Whitney U-test; n=8 per group. *p<0.05; **p<0.01. (E-F) Show examples of Hematoxylin-eosin and Resorcin-Fuchsin stained histological sections for detection of internal elastic lamina as black and visualization of the neointima and occlusion of arteries in control IgG and anti-Ang2 antibody treated groups, respectively. The Mann-Whitney U test was used to compare anti-Ang2 and IgG treatment. (Scale bar represents 20 μm). (G) Shows the results for quantification of the number of RECA-1+ stained vessels for control IgG and anti-Ang2 antibody treated groups. (H-I) Shows examples of RECA-1+ stained vessels for control IgG and anti-Ang2 antibody treated groups. n=8/group. Magnification 100×, inset 400×.

Example 5. Ex Vivo Intracoronary Perfusion with Anti-Ang2 Ab Reduces Cardiac Fibrosis and Allograft Vasculopathy in a Chronic Rejection Model The effects of ex vivo intracoronary perfusion with anti-Ang2 on cardiac fibrosis and allograft vasculopathy in a chronic rejection model was analyzed. Cardiac allografts were perfused with the anti-Ang2 antibody (MEDI1/5) or control IgG and subjected to 2-h preservation to analyze the effects of anti-Ang2 on cardiac fibrosis and allograft vasculopathy in a chronic rejection model with suboptimal cyclosporine A immunosuppression. Under suboptimal immunosuppression with CyA for 8 weeks after transplantation, the control allografts developed moderate cardiac fibrosis, which was significantly inhibited by perioperative intracoronary anti-Ang2 (MEDI1/5) treatment (FIG. 7A-C). In line with these findings, the Anti-Ang2 (MEDI1/5) treated allografts also had reduced arteriosclerosis compared to IgG-treated allografts (FIG. 7D-F). When analyzed 8 weeks after transplantation and compared to IgG-treated allografts, the perioperative ex vivo intracoronary Anti-Ang2 (MEDI1/5) treatment resulted in higher allograft capillary density, measured by quantifying myocardial RECA-1+ vessels (FIG. 7G-I).

These findings also emphasize the importance of early allograft protection. In a previous study with rat cardiac transplantations, CAV was shown to be more severe, if the allografts were subjected to preoperative hypothermic (cold) preservation (data not shown). Allograft ischemic time is also a known risk factor for mortality in human cardiac transplantation patients. The current results demonstrate that preoperative intracoronarily delivered single dose treatment with anti-Ang2 antibody significantly inhibited the development of cardiac fibrosis and vascular occlusion, observed 8 weeks after transplantation. These results show that inhibiting early microvascular dysfunction and IRI results in long-term protection of functional capillary network in rat cardiac allografts.

The current results demonstrate that perioperative treatment with an antibody against endogenous Ang2 prevented microvascular dysfunction and the development of cardiac fibrosis and allograft vasculpathy. These results support that inhibiting early microvascular dysfunction and IRI with anti-Ang2 treatment may have long-term effects in cardiac allografts.

Example 6. Human Organ Donor Brain Death and Cardiac Transplantation Causes Changes in Serum Ang2 Levels Human cardiac allograft donor and recipient blood samples were analyzed for serum Ang2 and Ang1. Organ donor brain death induces potentially cardiotoxic systemic cytokine storm (Venkateswaran R V, et al., Transplantation. 2009; 88:582-588). Samples from eleven cardiac allograft donors and recipients operated between 2010 and 2011 in Helsinki University Central Hospital, Helsinki, Finland were collected. The mean age of the recipients (8 men) was 47.4±11.4 years (range 29-63 years). The mean age of the donors (8 men) was 40.9±14.1 years (range 19-56 years). Healthy volunteers were used as a control group (n=24). The Ethical Committee of University of Helsinki, Helsinki, Finland approved the use of the patient samples.

Figure 8:
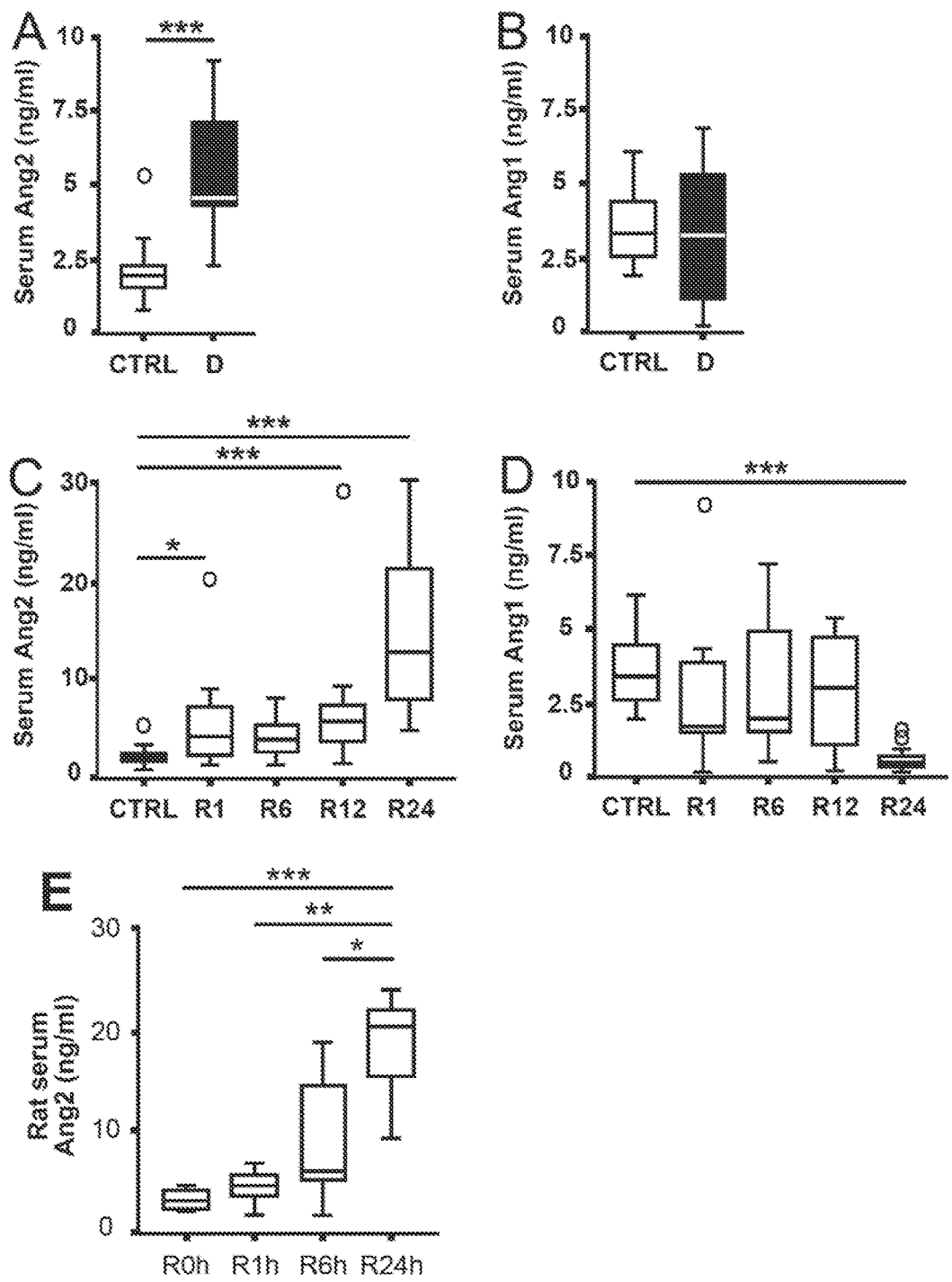
FIG. 8 shows Ang2 and Ang1 levels in serum from human cardiac allograft donors and recipients. (A-B) Shows Ang2 and Ang1 levels in patient serum samples from cardiac allograft donors (n=11) determined by enzyme-linked immunosorbent assay (ELISA) and compared to healthy controls (n=24). (C-D) Shows Ang2 and Ang1 levels in patient serum samples from cardiac allograft recipients (n=11) 1, 6, 12, and 24 h after transplantation determined by ELISA and compared to healthy controls (n=24). (E) Shows Ang2 levels in rat serum samples taken from cardiac allograft recipients and analyzed by ELISA preoperatively, 1, 6, 24 h after transplantation (n=8). The Mann-Whitney U test was used to compare the control group and the donor group (A and B). The Kruskall-Wallis test with Dunn correction was used to compare the control group with the recipient groups (C and D). Data are given by box plots showing the upper extreme (excluding outliers), upper quartile, median, lower quartile, and lower extreme (excluding outliers) (A-D): *P<0.05, ***P<0.001. Repeated measurements ANOVA was used to compare the sample groups (E): *P=0.0001, P=1.48E-5, *P=1.85E-7.

The serum levels of Ang2 or Ang1 were assessed in human cardiac allograft donors. Blood samples were collected preoperatively from cardiac allograft donors. Patient serum samples from cardiac allograft donors (n=11) were analyzed for Ang2 and Ang1 by enzyme-linked immunosorbent assay (ELISA) and compared to healthy controls (n=24). The Mann-Whitney U test was used to compare the control group and the donor group (FIG. 8A-B).

Patient serum samples from cardiac allograft recipients (n=11) 1, 6, 12, and 24 h after transplantation were analyzed for Ang2 and Ang1 by ELISA and compared to healthy controls (n=24). The Kruskall-Wallis test with Dunn correction was used to compare the control group with the recipient groups. Data were given by box plots showing the upper extreme (excluding outliers), upper quartile, median, lower quartile, and lower extreme (excluding outliers) (FIG. 8C-D).

ELISA analysis of the serum samples showed that the donor serum Ang2 levels were significantly higher than in the control group ($P<0.001$; FIG. 8A). The serum levels of Ang1 remained unchanged (FIG. 8B). The effects of cardiac transplantation on the serum levels of Ang2 and Ang1 were also tested. ELISA analysis showed that compared to the control group, Ang2 levels were significantly higher 1, 12 and 24 h after transplantation ($P<0.05$, $P<0.001$; FIG. 8C). The serum Ang1 levels were significantly lower in the recipients 24 h after transplantation ($P<0.001$; FIG. 8D).

Both the donors and the recipients had higher serum Ang2 levels than healthy controls. The Ang2 levels of allograft recipients increased gradually for up to 24 h after transplantation. These results show that human cardiac allograft donors had increased serum Ang2 levels and that cardiac transplantation resulted in increased serum Ang2 levels up to 24 h after transplantation. This Ang2 release in the donor after brain death can predispose the donated organs to injury and edema, even before organ recovery, hypothermic ischemic preservation, or reperfusion.

Ischemia-reperfusion injury after cardiac transplantation was also shown to increase the serum levels of Ang2 in rats. In particular, the kinetics of early Ang2 release was investigated in rat cardiac allografts. This assay was performed to help determine whether the Ang2 release seen in patient samples likely resulted from the ischemia-reperfusion injury, or from the alloimmune response. The kinetics of Ang2 release in rat was analyzed following fully MHC mismatched cardiac transplantations between DA donor and WF recipient rats without immunosuppression. Syngeneic and allogeneic cardiac transplantations were performed wherein DA donor rat hearts were recovered and subjected to 4-h cold preservation and then transplanted to either DA recipient rats, or to fully MHC-mismatched WF recipient rats without immunosuppression. Serum samples were repeatedly collected before, and 1, 6, and 24 h after cardiac transplantation. Repeated measures ANOVA with the Bonferroni correction revealed that serum levels of Ang2 gradually rose after reperfusion, peaking 24 h after transplantation (FIG. 8E). Similar to the human the patient samples, repeated measures ANOVA revealed significantly increased Ang2 serum levels of Ang2 in the recipients of rat cardiac allografts 6 and 24 h after transplantation. However, no Ang2 was detected in serum the recipients of syngenic cardiac allografts. These results suggested that the acute alloimmune response, and rather than the IRI, was the key inducer of Ang2 release after heart transplantation.

Example 7. Hypoxia-Mediated Lung Injury

Anti-Ang2 antibody (MEDI1/5) will be tested to determine if it can inhibit hypoxia-induced lung inflammation and injury. Reports suggests that hypoxia induces vascular leakage and inflammation (Eltzschig, H. K. & Carmeliet, P. Hypoxia and inflammation. N Engl J Med 364, 656-665 (2011); Eltzschig, H. K. & Eckle, T. Ischemia and reperfusion—from mechanism to translation. Nat Med 17, 1391-1401 (2011)). Angiopoietin-2 (Ang2), is considered as a vessel destabilizer and involved in inflammation and destabilization of cell-cell junctions (Augustin, H. G., Koh, G. Y., Thurston, G. & Alitalo, K. Control of vascular morphogenesis and homeostasis through the angiopoietin-Tie system. Nat Rev Mol Cell Biol 10, 165-177 (2009)).

Mice receiving ip injection of Ang2 blocking antibody or a control antibody and iv injection of Evan's Blue will be subjected to hypoxia in a hypoxia chamber supplied with 8% oxygen and 92% nitrogen. The lungs will be harvested and analyzed for Evan's Blue content. In an additional experiment, the lungs will be weighed and dried by Speed-Vac. The wet/dry weight ratio will be used to evaluate pulmonary edema.

Lungs will also be prepared for electron microscopy and histology, e.g., to see if the vessel junctions are stabilized by Ang2 blockade.

Lungs will be lysed and prepared for reverse-transcription PCR or Western blot analysis to determine whether Ang2 is upregulated and if junctional markers are downregulated during hypoxia, and whether Ang2 blocking antibody ameliorates the loss of junctional complexes. Lung lysates will also be subjected to proteomic analysis to detect differential signaling between Ang2 inhibition and control during hypoxia.

In converse experiments, transgenic mice overexpressing Ang2 by endothelial cells in an inducible manner will be analyzed similarly as above.

Example 8. Ischemic Stroke Injury

Anti-Ang2 antibody (MEDI1/5) will be tested to determine if it can inhibit and/or treat ischemic stroke injury in an animal model for stroke. Reports show that Ang-2 mediates differentiation and migration of neural progenitor cells in the subventricular zone after stroke (Liu et al., *JBC* 284(34): 22680-22689 (2009)).

Mice receiving ip injection of Ang2 blocking antibody or a control antibody before or after stroke injury will be subjected to the methods for modeling stroke as disclosed in Engel et al., Modeling Stroke in Mice—Middle Cerebral Artery Occlusion with the Filament Model. *J. Vis. Exp.* (47), e2423, DOI: 10.3791/2423 (2011).

In converse experiments, transgenic mice overexpressing Ang2 by endothelial cells in an inducible manner will be analyzed similarly as above.

Figure 9:
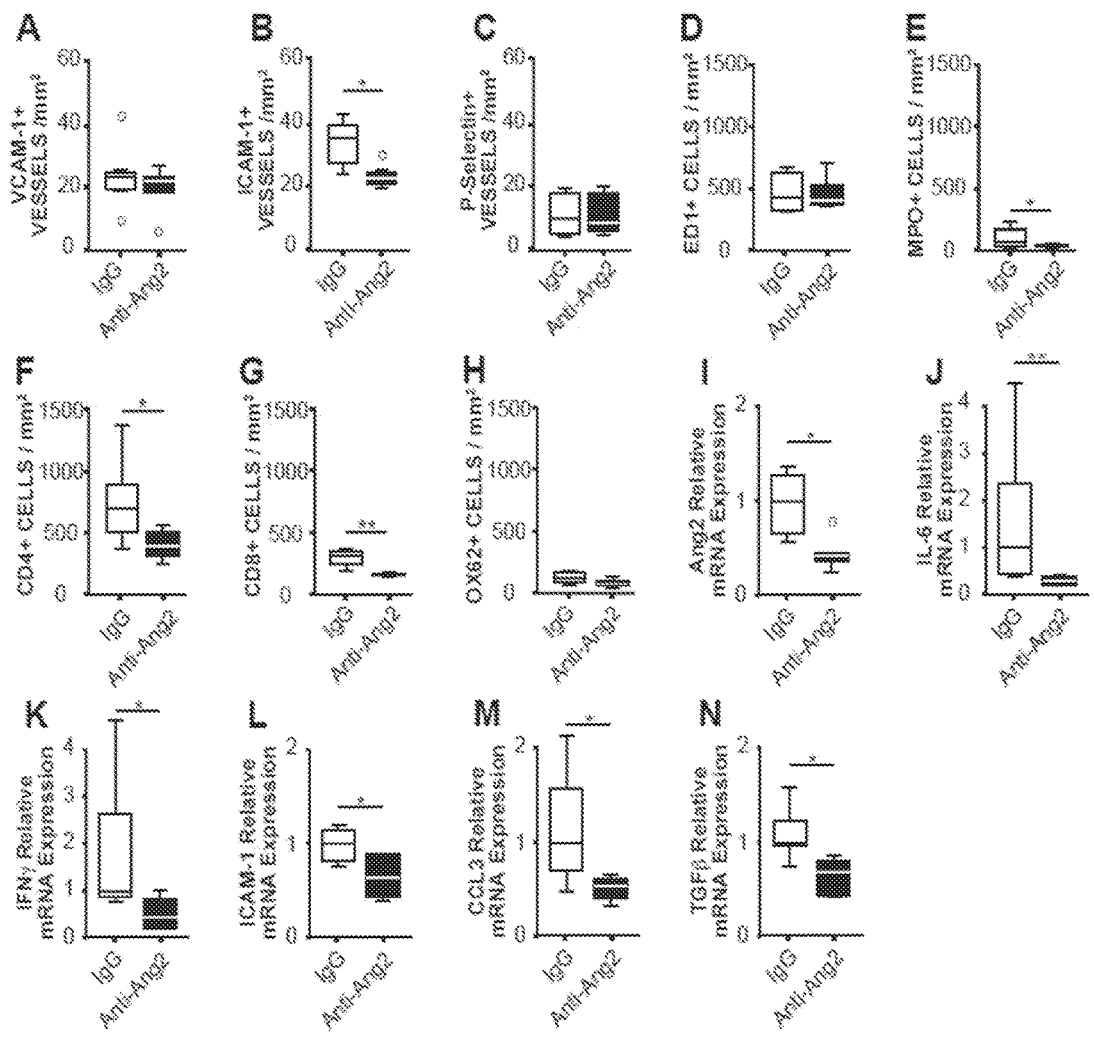
FIG. 9 shows ex vivo intracoronary treatment of rat cardiac allografts with anti-Ang2 antibody (MEDI1/5) prevented the development of acute rejection in 10 days and cardiac fibrosis and allograft vasculopathy in rat cardiac allografts 8 weeks after transplantation. (A-C) Shows the density of VCAM-1+, ICAM-1+, and P-selectin+ microvascular vessels in myocardial cross sections 10d after transplantation. (D-H) Shows the numbers of intragraft ED1+ macrophages, MPO+ neutrophils, CD4+ T cells, CD8+ T cells, and OX62+ dendritic cells 10d after transplantation. n=6 per group. (I-N) The relative mRNA expression of Ang2, IL-6, IFNγ, ICAM-1, CCL3, and TGFβ in allografts 10d after transplantation. (O) The survival of allografts in chronic rejection experiments. Data are given by Kaplan-Meier survival plot, or by box plots showing the upper extreme (excluding outliers), upper quartile, median, lower quartile, and lower extreme (excluding outliers). *P<0.05, **P<0.01 using the Mann-Whitney U test.
Figure 9:
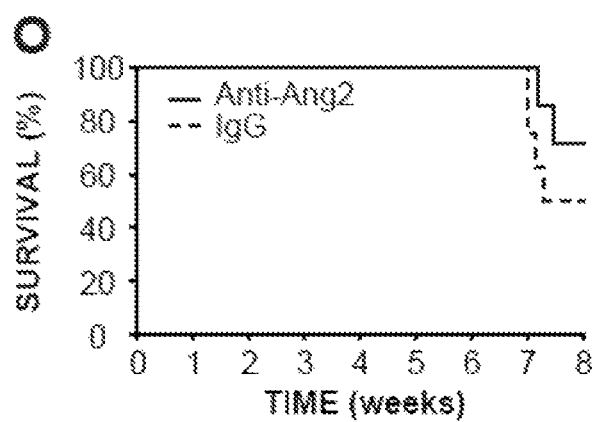
Figure 10:
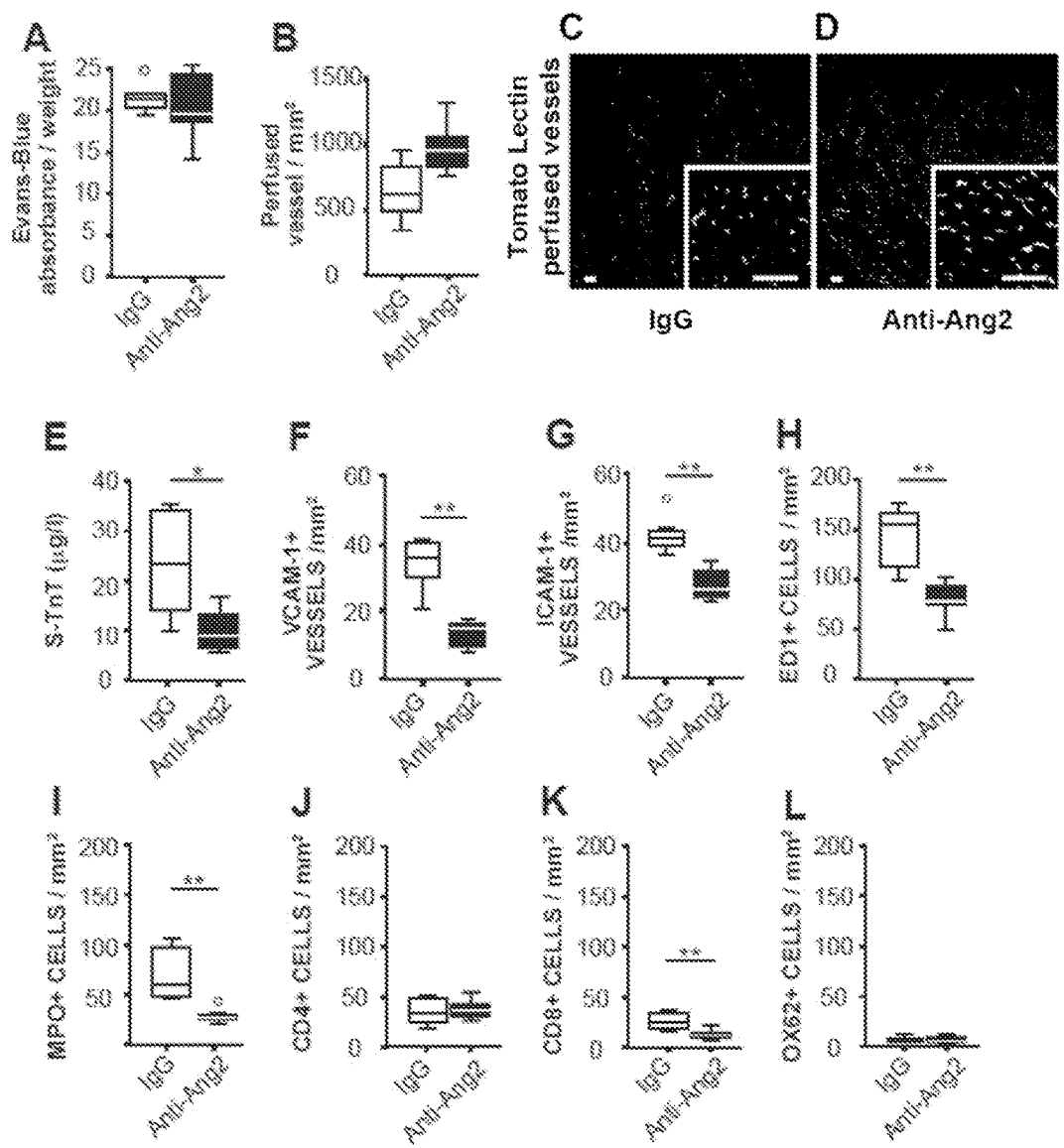
FIG. 10 shows cardiac allograft recipient treatment with anti-Ang2 antibody (MEDI1/5) does not prevent microvascular leakage or no-reflow phenomenon, but did prevent allograft myocardial injury, endothelial activation and inflammation 6 h after cardiac transplantation. The recipients received anti-Ang2 antibody (MEDI1/5) 4 h prior to the transplantation (1 mg/kg; i.p.). (A) Shows microvascular leakage measured by quantifying myocardial absorbance of extravasated Evans Blue dye 30 min after reperfusion (modified Miles assay). (B-D) Shows myocardial microvascular perfusion measured by quantifying the density of endothelium-binding FITC-labeled *Lycopersicon esculentum* lectin (green) 30 min after the reperfusion. (E) Shows the recipient serum levels of cardiomyocyte specific troponin T (TnT) 6 h after reperfusion. (F-G) Shows the density of VCAM-1+ and ICAM-1+. (H-L) Shows the numbers of intragraft ED1+ macrophages, MPO+ neutrophils, CD4+ T cells, CD8+ T cells, and OX62+ dendritic cells 6 h after reperfusion. n=6 per group. Magnification 100×, inset 400×; scale bars=50 μm (C and D). Data are given by box plots showing the upper extreme (excluding outliers), upper quartile, median, lower quartile, and lower extreme (excluding outliers). *P<0.05, **P<0.01, using the Mann-Whitney U test.

Example 9. Ex Vivo Intracoronary Treatment of Rat Cardiac Allografts with Anti-Ang2 Antibody Inhibits Acute and Chronic Rejection To study the effect of ex vivo intracoronary treatment with anti-Ang2 antibody (MEDI1/5) on acute rejection, transplantations in rats were performed as described above after 4-h cold preservation, but the recipient rats received a subtherapeutic dose of cyclosporine A immunosuppression (2 mg/kg/d for 7 days, and 1 mg/kg/d thereafter). The results are shown in FIGS. 9A-N. At 10 d—i.e. at the time of acute alloimmune activation—ex vivo anti-Ang2 antibody treatment significantly reduced the ICAM-1 immunoreactivity (FIG. 9B) and the numbers of allograft infiltrating MPO+ neutrophils, CD4+ and CD8+ T cells (FIG. 9E-G). In addition, ex vivo intracoronary treatment with anti-Ang2 antibody reduced the mRNA expression of Ang2, IL-6, IFN-γ, ICAM-1, CCL3, and TGFβ (FIG. 9I-N).

The effect of ex vivo intracoronary treatment with anti-Ang2 antibody (MEDI1/5) on cardiac fibrosis and allograft vasculopathy in a chronic rejection model was also analyzed. Because previous studies have indicated that 4-h preoperative cold preservation results in irreversible acute rejection and poor long-term allograft survival, 2-h cold preservation and a subtherapeutic dose of cyclosporine A immunosuppression was used in the chronic rejection analysis for this Example (Tuuminen R, Syrjälä et al., Donor Simvastatin Treatment Abolishes Rat Cardiac Allograft Ischemia/Reperfusion Injury and Chronic Rejection Through Microvascular Protection. Circulation. 2011). In this model, the allografts in both groups survived about equally as long (FIG. 9O) and were compared for histological changes (see FIG. 7A-I above).

These results show that Ang-2 had a prominent pro-inflammatory role immediately after transplantation and that inhibiting this response with anti-Ang2 antibody (MEDI1/5) resulted in long-term protection of cardiac allografts.

Example 10. Recipient Treatment with Single Dose of Anti-Ang2 Antibody Inhibits Ischemia-Reperfusion Injury by Anti-Inflammatory Function in Rat Cardiac Allografts Donor rat hearts were subjected to 4-h cold ischemia and the recipients received anti-Ang2 antibody (MEDI1/5) or control-IgG (1 mg/kg) i.p. 4 h before the transplantation. Modified Miles assay showed that the anti-Ang2 antibody did not protect the allograft from microvascular leakage and no-reflow phenomenon 30 min after the reperfusion (FIG. 10A-D).

The serum levels of Ang2 increased during the first day after the allograft transplantation, but not after syngraft transplantation, which shows that systemic recipient treatment with anti-Ang2 antibody would likely have an impact on early allograft inflammation. The allografts from DA donors were subjected to 4-h cold ischemia, and the WF recipients received anti-Ang2 antibody (MEDI1/5) or control-IgG (1 mg/kg) i.p. 4 h before the transplantation. This reduced the serum levels of TnT, the immunoreactivity of VCAM-1 and ICAM-1, and the number of allograft-infiltrating ED1+ macrophages, MPO+ neutrophils, and CD8+ T cells 6 h after the reperfusion, when compared to IgG-treated recipients (FIG. 10E-L).

Figure 11:
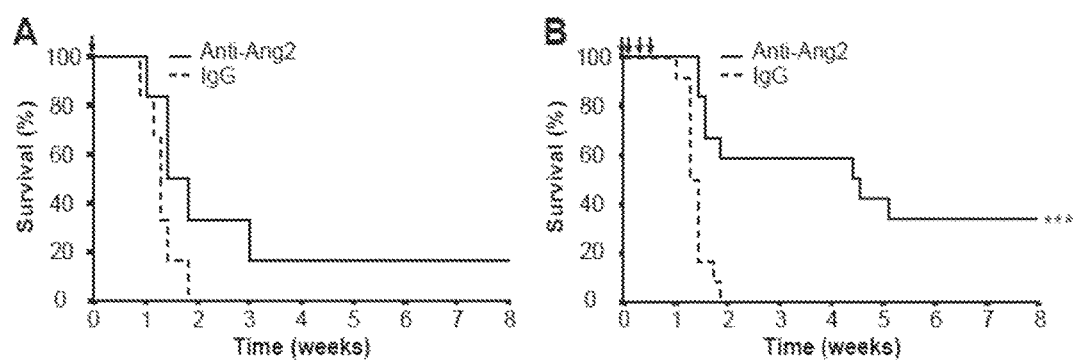
FIG. 11 shows cardiac allograft recipient treatment with multiple doses of anti-Ang2 antibody (MEDI1/5) prolongs allograft survival. (A) Shows the effect of single preoperative i.p. dose of anti-Ang2 antibody (1 mg/kg; black arrow) or IgG i.p. on allograft survival (n=6 per group). (B) Shows the effect multiple doses of anti-Ang2 antibody (1 mg/kg; black arrows) or IgG i.p. on allograft survival (n=12/group). Single dose was given 4 h before transplantation (A), and further consecutive doses were given on days 1, 3, and 5 after the transplantation (B). The recipients also received low-dose CyA (1 mg/kg/d s.c.). Data are given by Kaplan-Meier survival plot. ***P<0.001 using the Log-rank survival analysis.

Example 11. Recipient Treatment with Multiple Doses of Anti-Ang2 Antibody Prolongs the Survival of Rat Cardiac Allografts The effect of single and multiple anti-Ang2 antibody doses on allograft survival were compared to further explore the anti-inflammatory effects of recipient anti-Ang2 antibody treatment. The recipients received a very low dose of cyclosporine A (1 mg/kg/d s.c.) and either a single preoperative i.p. dose of anti-Ang2 antibody (MEDI1/5) or IgG, or 4 consecutive doses of anti-Ang2 antibody (MEDI1/5) or IgG 4 hour before transplantation, and 1, 3, and 5 days after the transplantation. Recipient treatment with single dose of anti-Ang2 antibody did not prolong cardiac allograft survival compared to the IgG-treated recipients (20.5±18.1 vs 10.2±2.3 days; FIG. 11A). However, multiple doses of anti-Ang2 antibody significantly prolonged allograft survival compared to the IgG-treated recipients (30.5±20.3 vs 9.6±1.5 days; FIG. 11B). These results show that Ang2 regulates inflammatory responses in cardiac allografts, in particular during the first days after transplantation, and administration of multiple doses of anti-Ang2 antibody to transplant recipients was able to prolonged allograft survival.

Although systemic treatment of allograft recipients with anti-Ang2 antibody 4 h before transplantation did not prevent microvascular leakage and the no-reflow phenomenon, the treatment significantly reduced allograft myocardial injury, microvascular endothelial cell activation, and inflammatory cell influx. Furthermore, when three consecutive doses of anti-Ang2 antibody were given during the following 5 days after transplantation, the allograft survival was prolonged and the development of cardiac fibrosis and allograft vasculopathy was prevented. Thus, in systemic recipient treatment, a multiple dose regimen of anti-angiopoietin-2 antibody produced beneficial long-term effects.

Figure 12:
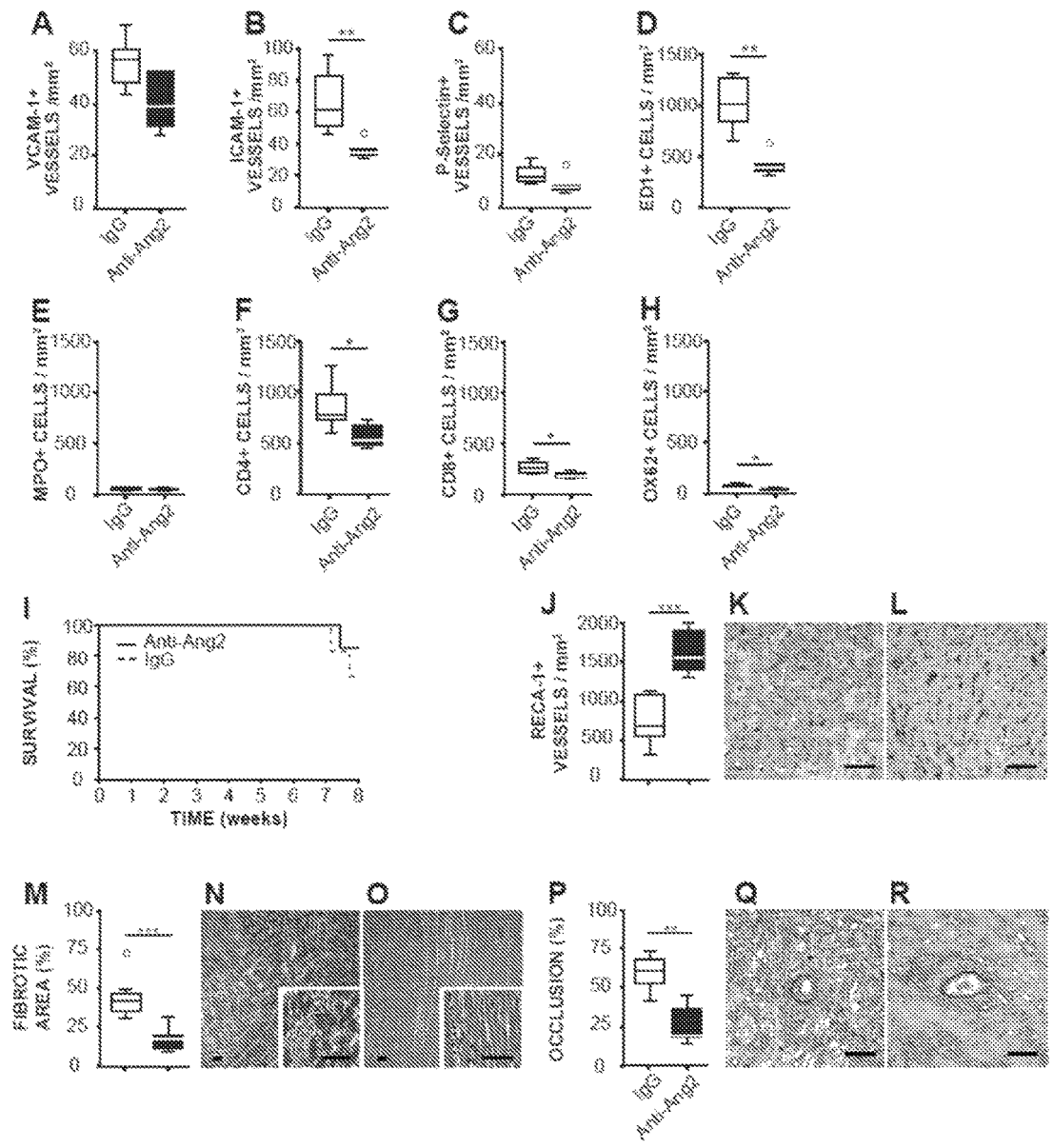
FIG. 12 shows cardiac allograft recipient treatment with multiple doses of anti-Ang2 antibody (MEDI1/5) prevents the development of acute rejection and cardiac fibrosis and allograft vasculopathy. (A-C) Shows the density of VCAM-1+, ICAM-1+, and P-selectin+ microvascular vessels in myocardial cross sections 10 days after transplantation. (D-H) Shows the numbers of intragraft ED1+ macrophages, MPO+ neutrophils, CD4+ T cells, CD8+ T cells, and OX62+ dendritic cells 10d after transplantation. n=6 per group. (I) Shows the survival of allografts in chronic rejection experiments. (J-L) Shows the numbers of RECA-1+ stained vessels 8 weeks after transplantation. (M-O) Shows the relative fibrotic area in Masson's trichrome stained mid-cardiac cross sections 8 weeks after transplantation. (P-R) Shows the degree of luminal occlusion in Hematoxylin-eosin and Resorcin-Fuchsin stained mid-cardiac cross sections 8 weeks after transplantation. n=6/group (A-H); n=7 per group (I-R). Magnification 100×, inset 400×; scale bars=50 μm (K, L, N, O, Q, and R). Data are given by Kaplan-Meier survival plot, or by box plots showing the upper extreme (excluding outliers), upper quartile, median, lower quartile, and lower extreme (excluding outliers). *P<0.05, **P<0.01 using the Mann-Whitney U test.

Example 12. Recipient Treatment with Multiple Doses of Anti-Ang2 Antibody Prevents Acute and Chronic Rejection in Rat Cardiac Allografts Multiple doses of anti-Ang2 antibody were tested to determine if this treatment modality could prevent acute rejection and the development of cardiac fibrosis and allograft vasculopathy in the chronic rejection model in rats. To assess the effect of recipient treatment on the alloimmune responses, the recipients received 4 consecutive i.p. doses of anti-Ang2 antibody (MEDI1/5) as above, plus subclinical immunosuppression with daily cyclosporine A (2 mg/kg/d for 7 days, and 1 mg/kg/d thereafter). Ten (10) days after the reperfusion, the recipient treatment with multiple doses of anti-Ang2 antibody significantly reduced the density of ICAM1+ capillaries, and the numbers of allograft infiltrating ED1+ macrophages, CD4+ and CD8+ T cells, and OX62+ dendritic cells (FIG. 12A-H). In chronic rejection experiments, the survival of the allografts was similar in both groups (FIG. 12I). Recipient treatment with multiple doses of anti-Ang2 antibody significantly increased the myocardial capillary density (FIG. 12J-L), and prevented the development of cardiac fibrosis and allograft vasculopathy 8 weeks after transplantation (FIGS. 12M-O and 12P-R).

Figure 13:
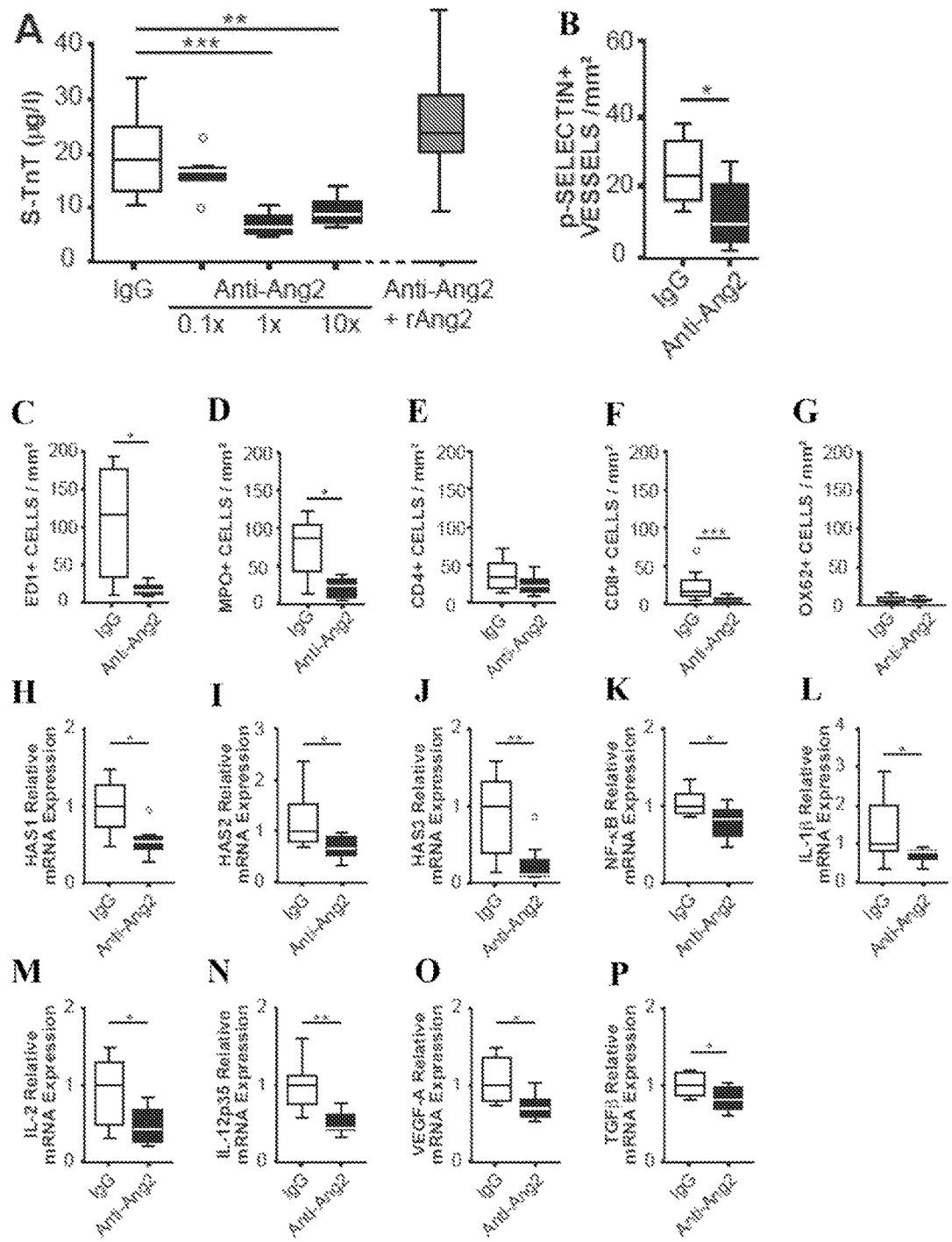
FIG. 13 shows ex vivo intracoronary treatment of rat cardiac allografts with anti-Ang2 antibody prevents myocardial injury and activation of innate immunity 6 h after transplantation. (A) Shows the dose-response analysis of the recipient serum levels of TnT 6 h after transplantation of anti-Ang2 antibody-perfused allografts, and of add-back experiments with combination of anti-Ang2 antibody (30 ng) and recombinant Ang2 (2 μg). (B) Shows the density of P-selectin+ microvascular vessels in myocardial cross sections 6 h after reperfusion. (C-G) Shows the numbers of intragraft ED1+ macrophages, MPO+ neutrophils, CD4+ T cells, CD8+ T cells, and OX62+ dendritic cells 6 h after reperfusion. (H-P) Shows the relative mRNA expression of HAS1-3, NF-kB, IL-1b, IL-2, IL-12p35, VEGF-A, and TGFb in allografts 6 h after transplantation. n=8 or 9/group. Data are given by box plots showing the upper extreme (excluding outliers), upper quartile, median, lower quartile, and lower extreme (excluding outliers). *P<0.05, P<0.01, *P<0.001 using the Mann-Whitney U test.

Example 13. Ex Vivo Intracoronary Treatment of Rat Cardiac Allografts with Anti-Ang2 Antibody Prevents Ischemia-Reperfusion Injury Via an Anti-Inflammatory Function The degree of allograft myocardial injury was assessed by measuring serum levels of cardiac troponin T (TnT) in serum 6 h after the transplantation. First, a dose-response analysis was performed, in which the ex vivo intracoronary treatment with anti-Ang2 antibody (MEDI1/5) with the dose of 3 ng/g (0.1×) of heart weight failed to inhibit acute myocardial injury, but the doses of 30 ng/g (1×) and 300 ng/g (10×) of heart weight reduced the serum levels of TnT significantly compared to IgG-treatment (FIG. 13A). Based on these results, the dose of 30 ng/g of heart weight was used in subsequent experiments.

To confirm the specificity of the anti-Ang2 antibody (MEDI1/5) in protection from ischemia-reperfusion injury, add-back experiments were performed in which anti-Ang2 antibody (30 ng/g MEDI1/5) in combination with rAng2 (2 μg/g) was administered. The results shows that rAng2 abrogated the positive result of the ex vivo intracoronary treatment with the anti-Ang2 antibody (FIG. 13A). As discussed above, the ex vivo intracoronary treatment of allografts with recombinant Ang2 (rAng2) alone did not affect microvascular leakage or no-reflow phenomenon 30 min after reperfusion, but rAng2 treatment induced severe myocardial injury and increased inflammatory cell influx when compared to the PBS-treatment (FIG. 4F-J).

Ex vivo intracoronary treatment of the allografts with the anti-Ang2 antibody significantly reduced vascular cell adhesion molecule-1 (VCAM-1), intracellular adhesion molecule-1 (ICAM-1), and P-selectin immunoreactivity in the microvasculature 6 h after the reperfusion, when compared to the IgG treatment (FIGS. 6G, 6J, and 13B). Furthermore, anti-Ang2 antibody treatment reduced the numbers of allograft infiltrating ED1+ macrophages, MPO+ neutrophils, and CD8+ T cells (FIGS. 13E, D, and F). In contrast, the numbers of allograft infiltrating CD4+ T cells or OX62+ dendritic cells were not changed (FIGS. 6E and G). These results show that anti-Ang2 antibody (MEDI1/5) treatment prevented the microvascular endothelial cell activation, accumulation of inflammatory cells, and innate immune activation in the allograft.

Figure 14:
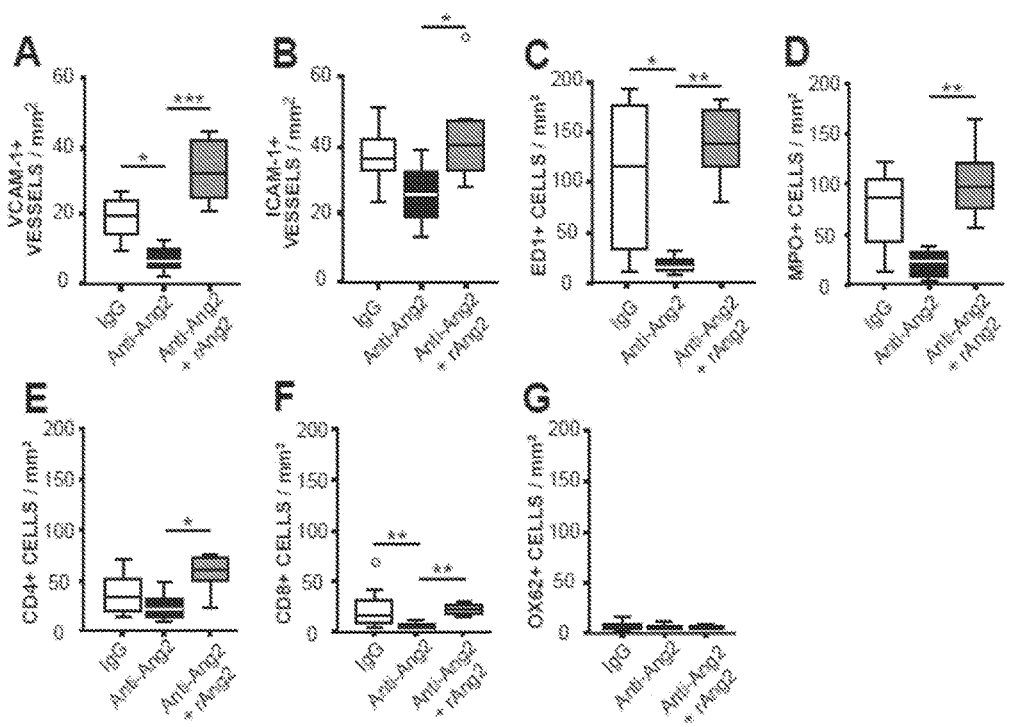
FIG. 14 shows that adding recombinant Ang2 to ex vivo intracoronary perfusion solution abrogates the protective effects of anti-Ang2 antibody 6 h after reperfusion. (A-B) Shows the density of VCAM-1+ and ICAM-1+ vessels in myocardial cross sections 6 h after reperfusion. (C-G) Shows the numbers of intragraft ED1+ macrophages, MPO+ neutrophils, CD4+ T cells, CD8+ T cells, and OX62+ dendritic cells 6 h after reperfusion. n=6 per group. Data are given by box plots showing the upper extreme (excluding outliers), upper quartile, median, lower quartile, and lower extreme (excluding outliers). *P<0.05, **P<0.01 using Kruskall-Wallis test with Dunn correction.

Ex vivo intracoronary treatment with rAng2 or—in add-back experiments—with rAng2 and anti-Ang2 antibody significantly increased the numbers of allograft infiltrating ED1+ macrophages and MPO+ neutrophils 6 h after the reperfusion, which correlated with greater myocardial injury in these groups (FIGS. 4F-J and 14A-G). Adding recombinant Ang2 to ex vivo intracoronary perfusion solution abrogated the protective effects of anti-Ang2 antibody 6 h after reperfusion. The density of VCAM-1+, ICAM-1+ vessels in myocardial cross sections 6 h after reperfusion are shown in FIG. 14A-B. The numbers of intragraft ED1+ macrophages, MPO+ neutrophils, CD4+ T cells, CD8+ T cells, and OX62+ dendritic cells 6 h after reperfusion are shown FIGS. 14C-G. Together, these results suggest that Ang2 had a pro-inflammatory role in IRI in cardiac allografts.

The results above show that early after reperfusion, regardless of the delivery method, anti-Ang2 antibody treatment significantly decreased the influx of graft-infiltrating macrophages, neutrophils, and CD8+ T cells early after the reperfusion.

III. Discussion

In vitro, hypoxia induced the deposition of Ang2-Tie2 complexes at endothelial cell-cell junctions. Ex vivo intracoronary perfusion with an Ang2 blocking antibody prevented destabilization of endothelial cell-cell junctions in coronary microvasculature during allograft preservation. Furthermore, ex vivo intracoronary perfusion with anti-Ang2 antibody reduced vascular leakage, no-reflow phenomenon, endothelial activation, inflammatory cell influx, myocardial injury, and innate immune activation in cardiac allografts after reperfusion. In a chronic rejection model, ex vivo intracoronary perfusion with anti-Ang2 antibody reduced adaptive immune response, cardiac fibrosis, and allograft vasculopathy and maintained myocardial capillary density.

The effect of intracoronarily delivered anti-Ang2 antibody on IRI-induced microvascular dysfunction and subsequent development of cardiac fibrosis and allograft vasculopathy in rat cardiac allografts was investigated. The results using an experimental cardiac transplantation model showed that anti-Ang2 antibody administration was advantageous for the protection of rat cardiac allografts from IRI. By injecting anti-Ang2 antibody into the coronaries via the clamped aortic root of a recovered heart, the disruption of vascular permeability associated with IRI and the subsequent myocardial damage was prevented. The results disclosed herein show a clinically feasible method of allograft protection with an intracoronarily administered single dose of endogenous Ang2 neutralizing anti-Ang2 antibody. Anti-Ang2 antibody therapy inhibited the IRI-induced microvascular dysfunction and subsequent development of cardiac fibrosis and chronic allograft vasculopathy. Single dose treatment with anti-Ang2 inhibited IRI-associated early innate immune activation by multiple parallel mechanisms and, furthermore, inhibited the development of subsequent cardiac fibrosis and CAV. These results show a clinically feasible strategy to protect cardiac allografts from primary and long-term allograft dysfunction, e.g., anti-Ang2 antibody use for clinical use in primary allograft protection as well as in perfusion solutions maintaining the endothelial integrity during the transplantation surgery.

These results show that Ang2 has a critical role in rat cardiac allograft IRI and microvascular dysfunction. Intracoronary perfusion with anti-Ang2 antibodies resulted in both primary and long-term allograft function improvement and protection from allograft dysfunction. These results support targeting the Ang1/Ang2 axis with anti-Ang2 antibody in protection of solid organ transplants. Furthermore, the results show preoperative ex vivo intracoronary perfusion with the anti-Ang2 antibody decreased IRI-associated vascular leakage, no-reflow phenomenon, cardiomyocyte damage, innate immune activation and subsequent development of cardiac fibrosis and allograft vasculopathy. These results show an important role for Ang2 in IRI and activation of innate and adaptive immune responses in cardiac allografts and support a clinically feasible, single ex vivo injection strategy to protect cardiac allografts from primary and long-term allograft dysfunction. The results highlight the role of Ang2 in regulating IRI-induced vascular dysfunction and support the use of anti-Ang2 antibody as a therapy for solid organ transplant protection.

In cardiac syngrafts, the primary IRI-induced neutrophil-intensive inflammation subsides during the first 24 h after heart the transplantation. However, in the cardiac allografts, the presence of CD8+ T cells prolongs the inflammatory response of neutrophils for up to three days after heart the transplantation. The results above show that early after reperfusion, regardless of the delivery method, anti-Ang2 antibody treatment significantly decreased the influx of graft-infiltrating macrophages, neutrophils, and, CD8+ T cells. These results further support a T cell-independent strategy to protect cardiac allografts with long-term beneficial effects.

The results herein show that the brain-death and the alloimmune response after transplantation induced the release of Ang2, and that ex vivo intracoronary treatment of rat cardiac allografts with anti-Ang2 blocking antibody prevented microvascular leakage and the no-reflow phenomenon. Furthermore, ex vivo intracoronary treatment of allografts and systemic recipient treatment with anti-Ang2 antibody inhibited the early innate and adaptive immune responses and the development of cardiac fibrosis and allograft vasculopathy. These results demonstrate the pivotal role of Ang2 in innate and adaptive immune responses after heart transplantation, and provide a clinically feasible strategy to prevent microvascular injury and the activation of innate immunity, and to protect cardiac allografts from the development of primary and long-term allograft failure using anti-Ang2 blocking antibody.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

REFERENCES

1. Davis S, Aldrich T H, Jones P F, Acheson A, Compton D L, Jain V, et al. Isolation of angiopoietin-1, a ligand for the TIE2 receptor, by secretion-trap expression cloning. Cell. 1996 Dec. 27; 87(7):1161-1169.
2. Maisonpierre P C, Suri C, Jones P F, Bartunkova S, Wiegand S J, Radziejewski C, et al. Angiopoietin-2, a natural antagonist for Tie2 that disrupts in vivo angiogenesis. Science. 1997 Jul. 4; 277(5322):55-60.
3. Jones N, Iljin K, Dumont D, Alitalo K. Tie receptors: new modulators of angiogenic and lymphangiogenic responses. Nat Rev Mol Cell Biol. 2001 Apr. 1; 2(4):257-267.
4. Jeansson M, Gawlik A, Anderson G, Li C, Kerjaschki D, Henkelman M, et al. Angiopoietin-1 is essential in mouse vasculature during development and in response to injury. J Clin Invest. 2011 Jun. 1; 121(6):2278-2289.
5. Augustin H G, Koh G Y, Thurston G, Alitalo K. Control of vascular morphogenesis and homeostasis through the angiopoietin-Tie system. Nat Rev Mol Cell Biol. 2009 March; 10(3):165-177.
6. Hanahan D. Signaling vascular morphogenesis and maintenance. Science. 1997 Jul. 4; 277(5322):48-50.
7. Zhang Z G, Zhang L, Croll S D, Chopp M. Angiopoietin-1 reduces cerebral blood vessel leakage and ischemic lesion volume after focal cerebral embolic ischemia in mice. Neuroscience. 2002; 113(3):683-687.
8. Cho C, Kammerer R, Lee H, Steinmetz M, Ryu Y, Lee S, et al. COMP-Ang1: a designed angiopoietin-1 variant with nonleaky angiogenic activity. Proc Natl Acad Sci USA. 2004 Apr. 13; 101(15):5547-5552.
9. Kim D, Jung Y, Lee A, Lee S, Kang K, Lee T, et al. COMP-angiopoietin-1 decreases lipopolysaccharide-induced acute kidney injury. Kidney Int. 2009 Dec. 1; 76(11):1180-1191.
10. Jung Y, Kim D, Lee A, Lee S, Kang K, Lee S, et al. Peritubular capillary preservation with COMP-angiopoietin-1 decreases ischemia-reperfusion-induced acute kidney injury. Am J Physiol Renal Physiol. 2009 Oct. 1; 297(4):F952-60.
11. Gamble J, Drew J, Trezise L, Underwood A, Parsons M, Kasminkas L, et al. Angiopoietin-1 is an antipermeability and anti-inflammatory agent in vitro and targets cell junctions. Circ Res. 2000 Sep. 29; 87(7):603-607.
12. Saharinen P, Eklund L, Miettinen J, Wirkkala R, Anisimov A, Winderlich M, et al. Angiopoietins assemble distinct Tie2 signalling complexes in endothelial cell-cell and cell-matrix contacts. Nat. Cell Biol. 2008 May; 10(5): 527-537.
13. Mammoto T, Parikh S M, Mammoto A, Gallagher D, Chan B, Mostoslaysky G, et al. Angiopoietin-1 requires p190 RhoGAP to protect against vascular leakage in vivo. J Biol Chem. 2007 Aug. 17; 282(33):23910-23918.
14. Kuo M-C, Patschan D, Patschan S, Cohen-Gould L, Park H-C, Ni J, et al. Ischemiainduced exocytosis of Weibel-Palade bodies mobilizes stem cells. J Am Soc Nephrol. 2008 Dec. 1; 19(12):2321-2330.
15. Pichiule P, Chavez J C, Lamanna J C. Hypoxic regulation of angiopoietin-2 expression in endothelial cells. J Biol Chem. 2004 Mar. 26; 279(13):12171-12180.
16. Oshima Y, Oshima S, Nambu H, Kachi S, Takahashi K, Umeda N, et al. Different effects of angiopoietin-2 in different vascular beds: new vessels are most sensitive. FASEB J. 2005 June; 19(8):963-965.
17. Yancopoulos G D, Davis S, Gale N W, Rudge J S, Wiegand S J, Holash J. Vascular-specific growth factors and blood vessel formation. Nature. 2000 Sep. 14; 407 (6801):242-248.
18. Tressel S L, Kim H, Ni C-W, Chang K, Velasquez-Castano J C, Taylor W R, et al. Angiopoietin-2 stimulates blood flow recovery after femoral artery occlusion by inducing inflammation and arteriogenesis. Arterioscler Thromb Vasc Biol. 2008 November; 28(11):1989-1995.

19. Reiss Y, Droste J, Heil M, Tribulova S, Schmidt M H H, Schaper W, et al. Angiopoietin-2 impairs revascularization after limb ischemia. Circ Res. 2007 Jul. 6; 101(1): 88-96.
20. Shyu K-G, Chang C-C, Wang B-W, Kuan P, Chang H. Increased expression of angiopoietin-2 and Tie2 receptor in a rat model of myocardial ischaemia/reperfusion. Clin Sci. 2003 Sep. 1; 105(3):287-294.
21. Dumitrescu C, Biondi R, Xia Y, Cardounel A, Druhan L, Ambrosio G, et al. Myocardial ischemia results in tetrahydrobiopterin (BH4) oxidation with impaired endothelial function ameliorated by BH4. Proc Natl Acad Sci USA. 2007 Sep. 18; 104(38):15081-15086.
22. Boros P, Bromberg J S. New cellular and molecular immune pathways in ischemia/reperfusion injury. Am J Transplant. 2006 April; 6(4):652-658.
23. Carden D, Granger D. Pathophysiology of ischaemia-reperfusion injury. J Pathol. 2000 Feb. 1; 190(3):255-266.
24. Goldstein D R. Toll-like receptors and other links between innate and acquired alloimmunity. Curr Opin Immunol. 2004 October; 16(5):538-544.
25. Walker W, Nasr I, Camirand G, Tesar B, Booth C, Goldstein D. Absence of innate MyD88 signaling promotes inducible allograft acceptance. J Immunol. 2006 Oct. 15; 177(8):5307-5316.
26. Gallagher D C, Bhatt R S, Parikh S M, Patel P, Seery V, McDermott D F, et al. Angiopoietin 2 is a potential mediator of high-dose interleukin 2-induced vascular leak. Clin. Cancer Res. 2007 Apr. 1; 13(7):2115-2120.
27. Tabruyn S P, Colton K, Morisada T, Fuxe J, Wiegand S J, Thurston G, et al. Angiopoietin-2-driven vascular remodeling in airway inflammation. Am J Pathol. 2010 December; 177(6):3233-3243.
28. Davis J S, Yeo T W, Piera K A, Woodberry T, Celermajer D S, Stephens D P, et al. Angiopoietin-2 is increased in sepsis and inversely associated with nitric oxide-dependent microvascular reactivity. Crit Care. 2010; 14(3):R89.
29. Yuan H T, Khankin E V, Karumanchi S A, Parikh S M. Angiopoietin 2 is a partial agonist/antagonist of Tie2 signaling in the endothelium. Mol Cell Biol. 2009 April; 29(8):2011-2022.
30. El-Sawy T, Miura M, Fairchild R. Early T cell response to allografts occurring prior to alloantigen priming upregulates innate-mediated inflammation and graft necrosis. Am J Pathol. 2004 July; 165(1):147-157.
31. El-Savvy T, Belperio J A, Strieter R M, Remick D G, Fairchild R L. Inhibition of polymorphonuclear leukocyte-mediated graft damage synergizes with short-term costimulatory blockade to prevent cardiac allograft rejection. Circulation. 2005 Jul. 19; 112(3):320-331.
32. Kim I, Moon S O, Park S K, Chae S W, Koh G Y. Angiopoietin-1 reduces VEGF-stimulated leukocyte adhesion to endothelial cells by reducing ICAM-1, VCAM-1, and E-selectin expression. Circ Res. 2001 Sep. 14; 89(6):477-479.
33. Witzenbichler B, Westermann D, Knueppel S, Schultheiss H-P, Tschope C. Protective role of angiopoietin-1 in endotoxic shock. Circulation. 2005 Jan. 4; 111(1):97-105.
34. Scholz A, Lang V, Henschler R, Czabanka M, Vajkoczy P, Chavakis E, et al. Angiopoietin-2 promotes myeloid cell infiltration in a {beta}2 integrin-dependent manner. Blood. 2011 Aug. 25;
35. Stehlik J, Edwards L B, Kucheryavaya A Y, Benden C, Christie J D, Dobbels F, et al. The Registry of the International Society for Heart and Lung Transplantation: Twenty-eighth Adult Heart Transplant Report-2011. J Heart Lung Transplant. 2011 October; 30(10):1078-1094.
36. Taylor A L, Watson C J E, Bradley J A Immunosuppressive agents in solid organ transplantation: Mechanisms of action and therapeutic efficacy. Crit Rev Oncol Hematol. 2005 October; 56(1):23-46.
37. Murphy S P, Porrett P M, Turka L A. Innate immunity in transplant tolerance and rejection. Immunol Rev. 2011 May; 241(1):39-48.
38. Tuuminen R, Syrjälä S, Krebs R, Keränen M A I, Koli K, Abo-Ramadan U, et al. Donor Simvastatin Treatment Abolishes Rat Cardiac Allograft Ischemia/Reperfusion Injury and Chronic Rejection Through Microvascular Protection. Circulation. 2011 Aug. 15.
39. Ono K, Lindsey E S. Improved technique of heart transplantation in rats. J Thorac Cardiovasc Surg. 1969 February; 57(2):225-229.
40. Hu X, Yee E, Harlan J M, Wong F, Karsan A. Lipopolysaccharide induces the antiapoptotic molecules, A1 and A20, in microvascular endothelial cells. Blood. 1998 Oct. 15; 92(8):2759-2765.
41. Jäättelä M, Mouritzen H, Elling F, Bastholm L. A20 zinc finger protein inhibits TNF and IL-1 signaling. J Immunol. 1996 Feb. 1; 156(3):1166-1173.
42. Gottlieb R A. Cell death pathways in acute ischemia/reperfusion injury. J. Cardiovasc. Pharmacol. Ther. 2011 August; 16(3-4):233-238.
43. Kevil C G, Payne D K, Mire E, Alexander J S. Vascular permeability factor/vascular endothelial cell growth factor-mediated permeability occurs through disorganization of endothelial junctional proteins. J Biol Chem. 1998 Jun. 12; 273(24):15099-15103.

What is claimed is:

1. A method for protecting a solid organ transplant tissue, comprising administering an effective amount of an anti-Angiopoietin-2 (Ang-2) antibody or antigen-binding fragment thereof to an allograft by perfusing the allograft with the antibody or antigen-binding fragment thereof wherein the antibody or antigen-binding fragment thereof comprises a variable heavy chain sequence comprising SEQ ID NO: 7 and a variable light chain sequence comprising SEQ ID NO: 3.

2. The method of claim 1, wherein the anti-Ang-2 antibody or antigen-binding fragment thereof neutralizes Ang-2.

3. The method of claim 1, wherein the anti-Ang-2 antibody or antigen-binding fragment thereof preferentially binds Ang-2 over Angiopoietin-1 (Ang-1).

4. The method of claim 1, wherein the anti-Ang-2 antibody or antigen-binding fragment thereof is an antibody that binds to and neutralizes Ang-2, but does not bind to Ang-1.

* * * * *

SEQUENCE LISTING

<160> NUMBER OF SEQ ID NOS: 8

<210> SEQ ID NO 1
<211> LENGTH: 215
<212> TYPE: PRT
<213> ORGANISM: Artificial
<220> FEATURE:
<223> OTHER INFORMATION: synthetic construct

<400> SEQUENCE: 1

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Thr Gly Ser
            20                  25                  30

```
Tyr Leu Ala Trp Tyr Gln Gln Lys Pro Gly Gln Ala Pro Arg Leu Leu
            35                  40                  45

Ile Cys Gly Ala Ser Ser Trp Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Ser Ser Ser Pro
                 85                  90                  95

Ile Thr Phe Gly Gln Gly Thr Arg Leu Glu Ile Lys Arg Thr Val Ala
            100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
            195                 200                 205

Ser Phe Asn Arg Gly Glu Cys
            210                 215

<210> SEQ ID NO 2
<211> LENGTH: 123
<212> TYPE: PRT
<213> ORGANISM: Artificial
<220> FEATURE:
<223> OTHER INFORMATION: Synthetic construct

<400> SEQUENCE: 2

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Thr Asn Tyr
             20                  25                  30

Gly Met His Trp Gly Arg Gln Ala Pro Gly Lys Gly Leu Glu Trp Val
            35                  40                  45

Ala Val Ile Ser His Asp Gly Asn Asn Lys Tyr Tyr Val Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Gly Ile Asp Phe Trp Ser Gly Leu Asn Trp Phe Asp Pro
            100                 105                 110

Trp Gly Gln Gly Thr Leu Val Thr Val Ser Ser
            115                 120

<210> SEQ ID NO 3
<211> LENGTH: 215
<212> TYPE: PRT
<213> ORGANISM: Artificial
<220> FEATURE:
<223> OTHER INFORMATION: Synthetic construct
```

<400> SEQUENCE: 3

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Thr Gly Ser
            20                  25                  30

Tyr Leu Ala Trp Tyr Gln Gln Lys Pro Gly Gln Ala Pro Arg Leu Leu
        35                  40                  45

Ile Thr Gly Ala Ser Ser Trp Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ser Ser Ser Pro
                85                  90                  95

Ile Thr Phe Gly Gln Gly Thr Arg Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 4
<211> LENGTH: 215
<212> TYPE: PRT
<213> ORGANISM: Artificial
<220> FEATURE:
<223> OTHER INFORMATION: Synthetic construct

<400> SEQUENCE: 4

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Thr Gly Ser
            20                  25                  30

Tyr Leu Ala Trp Tyr Gln Gln Lys Pro Gly Gln Ala Pro Arg Leu Leu
        35                  40                  45

Ile Asn Gly Ala Ser Ser Trp Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ser Ser Ser Pro
                85                  90                  95

Ile Thr Phe Gly Gln Gly Thr Arg Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu

```
            130                 135                 140
Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 5
<211> LENGTH: 215
<212> TYPE: PRT
<213> ORGANISM: Artificial
<220> FEATURE:
<223> OTHER INFORMATION: Synthetic construct

<400> SEQUENCE: 5

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Thr Gly Ser
                20                  25                  30

Tyr Leu Ala Trp Tyr Gln Gln Lys Pro Gly Gln Ala Pro Arg Leu Leu
            35                  40                  45

Ile Asp Gly Ala Ser Ser Trp Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ser Ser Ser Pro
                85                  90                  95

Ile Thr Phe Gly Gln Gly Thr Arg Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 6
<211> LENGTH: 215
<212> TYPE: PRT
<213> ORGANISM: Artificial
<220> FEATURE:
<223> OTHER INFORMATION: Synthetic construct

<400> SEQUENCE: 6
```

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Thr Gly Ser
            20                  25                  30

Tyr Leu Ala Trp Tyr Gln Gln Lys Pro Gly Gln Ala Pro Arg Leu Leu
        35                  40                  45

Ile Ala Gly Ala Ser Ser Trp Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ser Ser Ser Pro
                85                  90                  95

Ile Thr Phe Gly Gln Gly Thr Arg Leu Glu Ile Lys Arg Thr Val Ala
            100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 7
<211> LENGTH: 123
<212> TYPE: PRT
<213> ORGANISM: Artificial
<220> FEATURE:
<223> OTHER INFORMATION: Synthetic construct

<400> SEQUENCE: 7

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Thr Asn Tyr
            20                  25                  30

Gly Met His Trp Val Arg Gln Ala Pro Gly Lys Gly Leu Glu Trp Val
        35                  40                  45

Ala Val Ile Ser His Asp Gly Asn Asn Lys Tyr Tyr Val Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Ile Asp Phe Trp Ser Gly Leu Asn Trp Phe Asp Pro
            100                 105                 110

Trp Gly Gln Gly Thr Leu Val Thr Val Ser Ser
        115                 120

<210> SEQ ID NO 8
<211> LENGTH: 215
```

```
<212> TYPE: PRT
<213> ORGANISM: Artificial
<220> FEATURE:
<223> OTHER INFORMATION: Synthetic construct

<400> SEQUENCE: 8

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Thr Gly Ser
            20                  25                  30

Tyr Leu Ala Trp Tyr Gln Gln Lys Pro Gly Gln Ala Pro Arg Leu Leu
        35                  40                  45

Ile Thr Gly Ala Ser Ser Trp Ala Thr Gly Ile Ala Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ser Ser Ser Pro
                85                  90                  95

Ile Thr Phe Gly Gln Gly Thr Arg Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
            165                 170                 175

Ser Ser Thr Leu Thr Leu Ser Lys Ala Asp Tyr Glu Lys His Lys Val
        180                 185                 190

Tyr Ala Cys Glu Val Thr His Gln Gly Leu Ser Ser Pro Val Thr Lys
    195                 200                 205

Ser Phe Asn Arg Gly Glu Cys
    210                 215
```